(12) United States Patent
Klug et al.

(10) Patent No.: US 8,686,033 B2
(45) Date of Patent: Apr. 1, 2014

(54) PHOSPHORIC ACID ESTERS CONTAINING PHOSPHORUS ATOMS BRIDGED BY DIOL UNITS

(75) Inventors: Peter Klug, Grossostheim (DE); Franz-Xaver Scherl, Burgkirchen (DE); Waltraud Simsch, Kelkheim (DE); Adelgunde Oberhauser, Neuoetting (DE)

(73) Assignee: Clariant Finance (BVI) Limited, Tortola (VG)

( * ) Notice: Subject to any disclaimer, the term of this patent is extended or adjusted under 35 U.S.C. 154(b) by 432 days.

(21) Appl. No.: 12/671,422

(22) PCT Filed: Jul. 29, 2008

(86) PCT No.: PCT/EP2008/006218
§ 371 (c)(1),
(2), (4) Date: Sep. 22, 2010

(87) PCT Pub. No.: WO2009/015856
PCT Pub. Date: Feb. 5, 2009

(65) Prior Publication Data
US 2011/0003010 A1    Jan. 6, 2011

(30) Foreign Application Priority Data

Aug. 2, 2007  (DE) .......................... 10 2007 036 183
Jan. 31, 2008  (DE) .......................... 10 2008 006 855

(51) Int. Cl.
*A61K 33/42*  (2006.01)
*C07F 9/02*  (2006.01)

(52) U.S. Cl.
USPC .......................................... 514/506; 558/70

(58) Field of Classification Search
USPC .......................................................... 558/70
See application file for complete search history.

(56) References Cited

U.S. PATENT DOCUMENTS

| | | | |
|---|---|---|---|
| 2,895,787 | A | 7/1959 | Hall |
| 3,275,667 | A | 9/1966 | Bohunek et al. |
| 3,869,526 | A | 3/1975 | Combey et al. |
| 4,056,480 | A | 11/1977 | Herber |
| 4,180,532 | A | 12/1979 | Chakrabarti et al. |
| 4,220,611 | A | 9/1980 | Wolf |
| 5,192,462 | A | 3/1993 | Gloor et al. |
| 5,944,650 | A | 8/1999 | Hu et al. |
| 6,120,780 | A | 9/2000 | Dipuis et al. |
| 6,147,034 | A | 11/2000 | Jones et al. |
| 6,264,965 | B1 | 7/2001 | Roulier et al. |
| 6,448,297 | B1 | 9/2002 | Turowski-Wanke et al. |
| 2003/0219398 | A1 | 11/2003 | Loeffler et al. |
| 2003/0235598 | A1 | 12/2003 | Klug et al. |
| 2004/0068050 | A1 | 4/2004 | Miller et al. |
| 2004/0091558 | A1 | 5/2004 | Lutz et al. |
| 2004/0109835 | A1 | 6/2004 | Loffler et al. |
| 2005/0112081 | A1 | 5/2005 | Loeffler et al. |
| 2005/0113276 | A1 | 5/2005 | Taylor et al. |
| 2006/0069278 | A1 | 3/2006 | Stehr et al. |
| 2006/0153792 | A1 | 7/2006 | Arnaud et al. |
| 2007/0275854 | A1 | 11/2007 | Hess et al. |
| 2009/0004232 | A1 | 1/2009 | Brzokewicz |
| 2010/0260696 | A1 | 10/2010 | Klug et al. |
| 2010/0310483 | A1 | 12/2010 | Klug et al. |
| 2011/0040116 | A1 | 2/2011 | Klug et al. |
| 2011/0229427 | A1 | 9/2011 | Klug et al. |
| 2011/0230449 | A1 | 9/2011 | Klug et al. |

FOREIGN PATENT DOCUMENTS

| | | |
|---|---|---|
| DE | 35 42 441 | 6/1987 |
| DE | 100 16 875 | 10/2001 |
| DE | 10 2004 046 356 | 3/2006 |
| DE | 10 2004 047 092 | 3/2006 |
| EP | 0 510 246 | 10/1992 |
| EP | 0 816 403 | 1/1998 |
| EP | 1 005 857 | 6/2000 |
| EP | 1 344 517 | 9/2003 |
| EP | 1 344 518 | 9/2003 |
| EP | 1 352 644 | 10/2003 |
| EP | 1 407 813 | 4/2004 |
| EP | 1 514 537 | 3/2005 |
| EP | 1 518 900 | 3/2005 |
| GB | 2 023 606 | 1/1980 |
| JP | S49-057045 A | 6/1974 |
| JP | S51-149884 A | 12/1976 |
| JP | H07-157409 A | 6/1995 |
| JP | 09-020613 | 1/1997 |
| JP | 09-268193 | 10/1997 |

(Continued)

OTHER PUBLICATIONS

International Search Report for PCT/EP2008/006218 dated Jan. 14, 2010.

(Continued)

*Primary Examiner* — Shawquia Young
(74) *Attorney, Agent, or Firm* — Tod A. Waldrop

(57) ABSTRACT

Phosphoric esters comprise
A) one or more structural units derived from substances of component a), the substances of component a) being selected from orthophosphoric acid and one or more of its derivatives,
B) one or more structural units derived from substances of component b), the substances of component b) being selected from one or more compounds of formula (I)

$$R^2-O-(CH_2CH_2O)_u(C_3H_6O)_v(DO)_w-H \quad (I)$$

and
C) one or more structural units derived from substances of component c), the substances of component c) being selected from one or more diols of formula (II)

$$HO-(CH_2CH_2O)_a(C_3H_6O)_b(DO)_c-H \quad (II)$$

where the sum total a+b+c is ≥1, and the phosphoric ester contains 2 or more phosphorus atoms per molecule which are bridged via a structural unit derived from the compounds of formula (II).
The phosphoric esters of the invention are very useful in the manufacture of cosmetic, pharmaceutical and dermatological compositions.

21 Claims, No Drawings

(56) References Cited

FOREIGN PATENT DOCUMENTS

| | | |
|---|---|---|
| JP | H11-236592 A | 8/1999 |
| JP | 2000-178288 | 6/2000 |
| JP | 2005-535711 T | 11/2005 |
| JP | 2007-512356 T | 5/2007 |
| SU | 1435579 | 11/1988 |
| WO | WO 92/17159 | 10/1992 |
| WO | WO 97/19748 | 6/1997 |
| WO | WO 97/42252 | 11/1997 |
| WO | WO 98/00094 | 1/1998 |
| WO | WO 02/43689 | 6/2002 |
| WO | WO 2004/030605 | 4/2004 |
| WO | WO 2005/090366 | 9/2005 |
| WO | WO2005/102276 | 11/2005 |
| WO | WO2007/057598 | 5/2007 |
| WO | WO 2009/015858 | 2/2009 |

OTHER PUBLICATIONS

Translation of International Preliminary Report on Patentability for PCT/EP2008/006218, Jan. 14, 2010.
International Search Report for PCT/EP2008/006219 dated Jul. 6, 2009.
Translation of International Preliminary Report on Patentability for PCT/EP2008/006219, Jul. 6, 2009.
International Search Report for PCT/EP2008/006220, dated Jan. 15, 2009.
Translation of International Preliminary Report on Patentability for PCT/EP2008/006220, Jan. 15, 2009.
International Search Report for PCT/EP2008/006221 dated Jul. 9, 2009.
Translation of International Preliminary Report on Patentability for PCT/EP2008/006221, Jul. 9, 2009.
International Search Report for PCT/EP2008/006222 dated Jul. 6, 2009.
Translation of International Preliminary Report on Patentability for PCT/EP2008/006222, Jul. 6, 2009.
International Search Report for PCT/EP2009/000499 dated Dec. 21, 2009.
Translation of International Preliminary Report on Patentability for PCT/EP2009/000499, Dec. 21, 2009.
Database WPI Week 198921 Thomson Scientific, London, GB; AN 1989-157370 XP002533271 & SU 1 435 579 A (Macromolecular CPDS Inst) Nov. 7, 1988.
Database Chemabs Chemical Abstracts Service, Columbus, Ohio, US; 1984, Polkovnichenko, I.T. et al,: "Solubilizing power of alkyl ethoxy phospates" XP002533694.
English Abstract of DE 35 42 441, Jun. 4, 1987.
English Abstract of DE 100 16 875, Oct. 18, 2001.
English Abstract of EP 0 816 403, Jan. 7, 1998.
English Abstract of JP 2000-178288, Jun. 27, 2000.
English Abstract of JP 09-020613, Jan. 21, 1997.
English Abstract of JP 09-268193, Oct. 14, 1997.
English Abstract for JP 07-157409, Jun. 20, 1995.

PHOSPHORIC ACID ESTERS CONTAINING PHOSPHORUS ATOMS BRIDGED BY DIOL UNITS

This invention relates to esters formed from phosphoric acid or phosphoric acid derivatives, fatty alcohol, which is optionally alkoxylated, and diol, and also to their use as associative thickeners, particularly in cosmetic, pharmaceutical or dermatological compositions.

Cosmetic products have to meet high requirements. They shall have a clear appearance, be generally recognized as safe by toxicologists and ecotoxicologists, create a pleasant skin feel and have excellent rheological behavior which is constant over a wide pH range.

Water- or solvent-containing multicomponent systems such as emulsions or suspensions are frequently adjusted to higher viscosities, i.e., thickened, for economic reasons, for performance reasons or for stability reasons.

For instance, increasing the viscosity of the external or internal phase of emulsions or suspensions lengthens the time to separation of the components of such a system distinctly, which manifests itself in a lengthening of the storage time. Increasing the viscosity also improves for many products their uniform distributability on nonplanar surfaces in particular.

The more uniform distribution and lengthened active time enhances the efficacy. In addition to the performance advantages mentioned, the high viscosity of such products also offers further advantages in relation to manufacture, packaging, filling and storage and also in transportation.

The technical literature contains reports of a large number of different systems for adjusting the rheological properties of aqueous or solvent-containing systems, emulsions or suspensions. Known examples are cellulose ethers and other cellulose derivatives (for example carboxymethylcellulose, hydroxyethylcellulose), gelatin, starch and starch derivatives, sodium alginates, fatty acid polyethylene glycol esters, agar, tragacanth or dextrins. By way of synthetic polymers, various materials are used, examples being polyvinyl alcohols, polyacrylamides, polyacrylic acid and various salts of polyacrylic acid, polyvinylpyrrolidone, polyvinyl methyl ether, polyethylene oxides, copolymers of maleic anhydride and vinyl methyl ether, and also diverse mixtures and copolymers thereof.

However, the compounds mentioned display manifold disadvantages in use. For instance, cellulose derivatives and, in general, materials based on natural raw materials and the formulations resulting therefrom are very vulnerable to bacteria. Technically, they usually form unpleasant, "ropey" gels. Fatty acid polyethylene glycol esters tend to hydrolyze in the presence of water and the resulting insoluble fatty acids cause undesirable clouding. Thickeners of natural origin (for example agar or tragacanth) fluctuate substantially in composition, depending on provenience.

U.S. Pat. No. 5,129,462 describes shampoo formulations comprising polyethylene glycol polyol fatty acid esters, particularly PEG pentaerythritol fatty acid esters as thickeners. The processing and formulatability of this class of compounds is impaired by their high melting points or setting points.

EP 1 518 900 and EP 1 344 518 disclose cosmetic and pharmaceutical preparations comprising oxyalkylated polyglycerol esters as thickeners, dispersants for aqueous, aqueous-alcoholic and aqueous-surfactant preparations and as emulsifiers, suspending agents having a thickening effect and consistency regulators for emulsions and suspensions.

The associative thickeners described in the references cited still have room for improvement with regard to their thickening performance, specifically in purely aqueous systems, where they only form cloudy gels, but also with regard to their stability at low pH. At below pH 5 their gels and thickened surfactant solutions are not stable in storage, but very rapidly lose viscosity.

It is an object of the present invention to provide a novel class of substances which is suitable for use in cosmetic products, gives a clear appearance in the formulations and even in a very acidic medium engenders a high thickening capacity in the event of thermal stress and long storage times, and combines these properties with excellent thickening performance.

We have found that this object is achieved, surprisingly, by esters of phosphoric acid or esters of phosphoric acid derivatives with optionally alkoxylated fatty alcohols, the esters being characterized in that the phosphorus atoms are bridged via groups derived from diols.

The present invention accordingly provides phosphoric esters comprising

A) one or more structural units derived from substances of component a), the substances of component a) being selected from orthophosphoric acid and one or more of its derivatives and the one or more derivatives of orthophosphoric acid preferably being selected from polyphosphoric acid, tetraphosphorus decaoxide, phosphoryl chloride and phosphorus pentachloride, B) one or more structural units derived from substances of component b), the substances of component b) being selected from one or more compounds of formula (I)

$$R^2-O-(CH_2CH_2O)_u(C_3H_6O)_v(DO)_w-H \qquad (I)$$

where $R^2$ is a linear or branched, saturated alkyl group having 6 to 30, preferably 8 to 22 and more preferably 12 to 18 carbon atoms, or is a linear or branched mono- or polyunsaturated alkenyl group having 6 to 30, preferably 8 to 22 and more preferably 12 to 18 carbon atoms, D is a linear or branched saturated alkylene group having 4 to 20 carbon atoms, is a linear or branched mono- or polyunsaturated alkenylene group having 4 to 20 carbon atoms or is —CH(aryl)CH$_2$—, preferably —CH(phenyl)CH$_2$—, u is a number from 0 to 200, preferably from 2 to 150, more preferably from 5 to 100 and even more preferably from 10 to 50, v is a number from 0 to 100, preferably from 0 to 50 and more preferably from 0 to 20, w is a number from 0 to 100, preferably from 0 to 20 and more preferably from 0 to 10, and where the groups CH$_2$CH$_2$O, C$_3$H$_6$O and DO from the compounds of formula (I) can be arranged blocklike or randomly distributed, and C) one or more structural units derived from substances of component c), the substances of component c) being selected from one or more diols of formula (II)

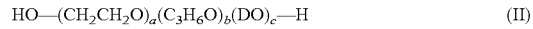

$$HO-(CH_2CH_2O)_a(C_3H_6O)_b(DO)_c-H \qquad (II)$$

where

D is as defined in formula (I), a is a number from 0 to 800, preferably from 0 to 250, more preferably from 10 to 200 and even more preferably from 20 to 100, b is a number from 0 to 100 and preferably from 0 to 50, c is a number from 0 to 100 and preferably from 0 to 20, where the sum total a+b+c is ≥1, preferably from 5 to 150, and the groups $CH_2CH_2O$, $C_3H_6O$ and DO from the compounds of formula (II) can be arranged blocklike or randomly distributed, and
the phosphoric esters contain 2 or more phosphorus atoms per molecule which are bridged via a structural unit derived from the compounds of formula (II).

The phosphoric esters of the present invention comprise at least 2 phosphorus atoms and may have a linear or branched structure from 4 phosphorus atoms onward.

In the phosphoric esters of the present invention, the structural units derived from substances of component b) selected from the compounds of formula (I) conform to formula (I')

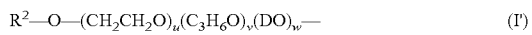   (I')

where
$R^2$, D, u, v and w are each as defined above under formula (I).

In the phosphoric esters of the present invention, the structural units derived from substances of component c) selected from the compounds of formula (II) conform to formula (II')

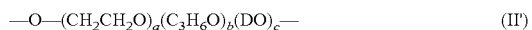   (II')

where
a, b, c and D are each as defined above under formula (II).

It is essential to the present invention that the phosphoric esters of the present invention each comprise at least one structural unit derived from substances of component a), at least one structural unit as per formula (I') and at least one structural unit as per formula (II').

The phosphoric esters of the present invention do not contain any oxygen-oxygen bond —O—O—. The structural units derived from the substances of components a), b) and c) are bonded to each other via one oxygen atom —O— only.

For example, a substructure of a phosphoric ester of the present invention in which in each case a structural unit derived from substances of components b) and c) is bonded to a structural unit derived from the substances of component a) and wherein the structural unit derived from the substances of component a) has the structure

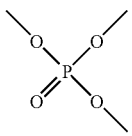

would have the following structure

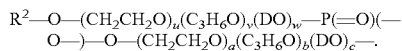

If, for example, this substructure had u=1, v=w=0, a=1 and b=c=0, the structure would look as follows:

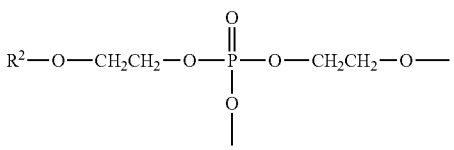

There is no oxygen-oxygen bond in this structural unit.

In one preferred embodiment of the present invention, the number of structural units derived from substances of component b) per molecule of phosphoric ester is 2 or more and preferably 3 or more.

In a further preferred embodiment of the present invention, $R^2$ is a linear or branched saturated alkyl group having 6 to 30, preferably 8 to 22 and more preferably 12 to 18 carbon atoms.

In a further preferred embodiment of the present invention, at least 80%, preferably from 90 to 100% and more preferably from 95 to 100% of the maximum number of esterifiable functions in the phosphoric esters theoretically obtainable from the substances of component a) are in an esterified state.

The remaining free valences on the phosphorus atom, i.e., the esterifiable functions which are not esterified, can be acid groups P—OH, but also groups of the form P—O counter ion, in which case the counter ions are selected from $Li^+$, $Na^+$, $K^+$, $Mg^{++}$, $Ca^{++}$, $Al^{+++}$, $NH_4^+$ and quaternary ammonium ions $[HNR^1R^2R^3]^+$, where $R^1$, $R^2$ and $R^3$ independently can be hydrogen, a linear or branched alkyl group having 1 to 22 carbon atoms, a linear or branched mono- or polyunsaturated alkenyl group having 2 to 22 carbon atoms, a linear monohydroxyalkyl group having 2 to 10 carbon atoms, preferably a monohydroxyethyl or monohydroxypropyl group, and also a linear or branched dihydroxyalkyl group having 3 to 10 carbon atoms.

The degree of neutralization of the nonesterified phosphorus valences (P—OH) in the phosphoric esters of the present invention can be between 0% and 100%. In one preferred embodiment of the present invention, the degree of neutralization is from 0-20%. In another preferred embodiment of the invention, the degree of neutralization is from 20.1-100%.

In a further preferred embodiment of the present invention, v and w in the structural units derived from the compounds of formula (I) are 0.

In a further preferred embodiment of the present invention, u in the structural units derived from the compounds of formula (I) is in the range from 1 to 150, preferably in the range from 5 to 100 and more preferably in the range from 10 to 50.

In a further preferred embodiment of the present invention, b and c in the structural units derived from the compounds of formula (II) are 0.

In a further preferred embodiment of the present invention, a in the structural units derived from the compounds of formula (II) is in the range from 1 to 800, preferably in the range from 10 to 200 and more preferably in the range from 20 to 100.

In a further preferred embodiment of the present invention, the one or more structural units derived from the one or more diols of formula (II) are derived from diols selected from ethylene glycol, diethylene glycol, triethylene glycol, tetraethylene glycol, polyethylene glycol (PEG) having molecular weights from 200 to 35 000, preferably PEG 200, PEG 300, PEG 400, PEG 600, PEG 800, PEG 1000, PEG 1500, PEG 2000, PEG 3000, PEG 3350, PEG 4000, PEG 6000, PEG 8000, propylene glycol, dipropylene glycol, tripropylene glycol, polypropylene glycol, polybutylene glycol, copolymers of ethylene oxide and propylene oxide having molecular weights of 200 to 35 000, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol and 1,12-dodecanediol.

In a further preferred embodiment of the present invention, the one or more structural units derived from the one or more compounds of formula (I) are structural units wherein u is a number from 1 to 200, preferably from 2 to 150, more preferably from 5 to 100 and even more preferably from 10 to 50, v and w are 0 and the radical $R^2$—O— is derived from alcohols selected from octanol, decanol, dodecanol, tetradecanol, hexadecanol, octadecanol, eicosanol, behenyl alcohol, fatty alcohols having C-chain cuts between 8 and 22, preferably $C_{10}/C_{12}$ fatty alcohol, $C_{12}/C_{14}$ fatty alcohol, $C_{12}/C_{15}$ fatty alcohol and $C_{16}/C_{18}$ fatty alcohol, branched fatty alcohols, preferably Guerbet alcohols and monounsaturated fatty alcohols, preferably delta-9-cis-hexadecanol, delta-9-cis-octadecanol, trans-9-octadecanol and cis-delta-11-octadecanol.

In a particularly preferred embodiment of the present invention, the one or more structural units derived from the one or more compounds of formula (I) are structural units derived from $C_{16/18}$ fatty alcohol ethoxylates with 10-50 ethylene oxide units, preferably structural units derived from substances selected from $C_{16/18}$ fatty alcohol ethoxylate with 11 ethylene oxide units, $O_{16/18}$ fatty alcohol ethoxylate with 25 ethylene oxide units and $C_{16/18}$ fatty alcohol ethoxylate with 50 ethylene oxide units.

In a further particularly preferred embodiment of the present invention, the total number of the structural units in the phosphoric ester which are derived from the one or more compounds of formula (I), preferably the total number of the structural units in the phosphoric ester which are derived from the one or more compounds of formula (I) wherein u is a number from 1 to 200, preferably from 2 to 150, more preferably from 5 to 100 and even more preferably from 10 to 50 and v and w are 0 is in the range from 4 to 20, preferably in the range from 4 to 10 and more preferably in the range from 4 to 6.

In a further preferred embodiment of the present invention, the total number in the phosphoric esters of ethylene oxide units in the structural units derived from the substances of component b) and the substances of component c) is together in the range from 30 to 100 and preferably in the range from 40 to 80 per fatty alcohol end group emerged from the compounds of formula (I).

In further preferred phosphoric esters of the present invention, the structural units derived from the substances of component a) are selected from structural units of formulae (A1) to (A3)

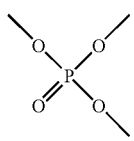

(A1)

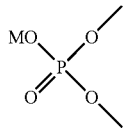

(A2)

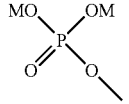

(A3)

where
M in each occurrence independently is $H^+$ or a counter ion and the counter ions are selected from $Li^+$, $Na^+$, $K^+$, $Mg^{++}$, $Ca^{++}$, $Al^{+++}$ $NH_4^+$ and quaternary ammonium ions $[HNR^1R^2R^3]^+$, where $R^1$, $R^2$ and $R^3$ independently can be hydrogen, a linear or branched alkyl group having 1 to 22 carbon atoms, a linear or branched mono- or polyunsaturated alkenyl group having 2 to 22 carbon atoms, a linear monohydroxyalkyl group having 2 to 10 carbon atoms, preferably a monohydroxyethyl or monohydroxypropyl group, and also a linear or branched dihydroxyalkyl group having 3 to 10 carbon atoms,
and preferably are structural units of formula (A1).

In a further preferred embodiment of the present invention, the phosphoric esters consist of structural units derived from the substances of components a), b) and c).

In a further preferred embodiment of the present invention, the phosphoric esters of the present invention are selected from compounds of formula (III)

where
E is a group of formula (IIIa)

V is a group of formula (IIIb)

M is a group of formula (IIIc)

$R^a$ in each occurrence independently are —OH, —OS or radicals of formula)(I')

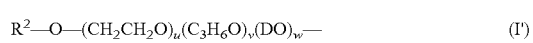

where
S is a counter ion,
$R^2$ is a linear or branched, saturated alkyl group having 6 to 30, preferably 8 to 22 and more preferably 12 to 18 carbon atoms or is a linear or branched, mono- or polyunsaturated alkenyl group having 6 to 30, preferably 8 to 22 and more preferably 12 to 18 carbon atoms,
D is a linear or branched saturated alkylene group having 4 to 20 carbon atoms, is a linear or branched mono- or polyunsaturated alkenylene group having 4 to 20 carbon atoms or is —CH(aryl)CH$_2$—, preferably —CH(phenyl)CH$_2$—,
u is a number from 0 to 200, preferably from 2 to 150, more preferably from 5 to 100 and even more preferably from 10 to 50,
v is a number from 0 to 100, preferably from 0 to 50 and more preferably from 0 to 20,
w is a number from 0 to 100, preferably from 0 to 20 and more preferably from 0 to 10, and
where the groups $CH_2CH_2O$, $C_3H_6O$ and DO from the radicals of formula (I') can be arranged blocklike or randomly distributed, Q in each occurrence independently are radicals of formula (II')

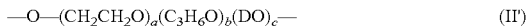

$$—O—(CH_2CH_2O)_a(C_3H_6O)_b(DO)_c— \qquad (II')$$

where
D is as defined in formula (I'),
a is a number from 0 to 800, preferably from 0 to 250, more preferably from 10 to 200 and even more preferably from 20 to 100,
b is a number from 0 to 100 and preferably from 0 to 50,
c is a number from 0 to 100 and preferably from 0 to 20,
where the sum total a+b+c is ≥1, preferably from 5 to 150, and the groups $CH_2CH_2O$, $C_3H_6O$ and DO from the compounds of formula (II') can be arranged blocklike or randomly distributed, and
x is a number from 0 to 10, preferably 0 to 5 and more preferably 0 to 3, and
y is a number from 0 to 10, preferably 0 to 5 and more preferably 0 to 3,
with the proviso that the number of radicals of formula (I') in the phosphoric esters of formula (III) is not less than 1, preferably not less than 2 and more preferably not less than 3.

The phosphoric esters of formula (III) have no structural units -Q-Q-, i.e., whenever two structural units selected from formulae (IIIa), (IIIb) and (IIIc) meet, there is only one group Q between the two structural units.

The simplest structure of formula (III) would be for x=0 and y=0 a structure of the formula $E_2V_0M_0$. The formula $E_2V_0M_0$ can also be represented by the following structural formula formed from two structural units of formula (IIIa):

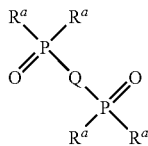

It is again apparent from this structural formula that there is only one single group Q bonded between the two structural units of formula (IIIa).

Preferred embodiments of the phosphoric esters of formula (III) will now be described.

Preferably, $R^2$ in the radicals of formula (I') is a linear or branched, saturated alkyl group having 6 to 30, preferably 8 to 22 and more preferably 12 to 18 carbon atoms.

Further preferred phosphoric esters of formula (III) are those wherein at least 80%, preferably from 90 to 100% and more preferably from 95 to 100% of the esterifiable functions bonded directly to the phosphorus atoms P are esterified.

The degree of neutralization of the nonesterified phosphorus valences in the phosphoric esters of formula (III) can be between 0% and 100%. In one preferred embodiment of the present invention, the degree of neutralization is from 0-20%. In another preferred embodiment of the present invention, the degree of neutralization is from 20.1-100%.

Preferred counter ions S in the phosphoric esters of formula (III) are selected from $Li^+$, $Na^+$, $K^+$, $Mg^{++}$, $Ca^{++}$, $Al^{+++}$, $NH_4^+$ and quaternary ammonium ions $[HNR^1R^2R^3]^+$, where $R^1$, $R^2$ and $R^3$ independently can be hydrogen, a linear or branched alkyl group having 1 to 22 carbon atoms, a linear or branched mono- or polyunsaturated alkenyl group having 2 to 22 carbon atoms, a linear monohydroxyalkyl group having 2 to 10 carbon atoms, preferably a monohydroxyethyl or monohydroxypropyl group, and also a linear or branched dihydroxyalkyl group having 3 to 10 carbon atoms.

Further preferred phosphoric esters of formula (III) are those wherein v and w in the radicals of formula (I') are 0.

Further preferred phosphoric esters of formula (III) are those wherein u in the radicals of formula (I') is in the range from 1 to 150, preferably in the range from 5 to 100 and more preferably in the range from 10 to 50.

Further preferred phosphoric esters of formula (III) are those wherein b and c in the radicals of formula (II') are 0.

Further preferred phosphoric esters of formula (III) are those wherein a in the radicals of formula)(II') is in the range from 1 to 800, preferably in the range from 10 to 200 and more preferably in the range from 20 to 100.

Further preferred phosphoric esters of formula (III) are those wherein the one or more radicals of formula (II') are derived from diols selected from ethylene glycol, diethylene glycol, triethylene glycol, tetraethylene glycol, polyethylene glycol (PEG) having molecular weights from 200 to 35 000, preferably PEG 200, PEG 300, PEG 400, PEG 600, PEG 800, PEG 1000, PEG 1500, PEG 2000, PEG 3000, PEG 3350, PEG 4000, PEG 6000, PEG 8000, propylene glycol, dipropylene glycol, tripropylene glycol, polypropylene glycol, polybutylene glycol, copolymers of ethylene oxide and propylene oxide having molecular weights of 200 to 35 000, 1,2-butanediol, 1,3-butanediol, 1,4-butanediol, 1,2-pentanediol, 1,3-pentanediol, 1,4-pentanediol, 1,5-pentanediol, 1,2-hexanediol, 1,3-hexanediol, 1,4-hexanediol, 1,5-hexanediol, 1,6-hexanediol and 1,12-dodecanediol.

Further preferred phosphoric esters of formula (III) are those wherein u in the radicals of formula (I') is in the range from 1 to 200, preferably in the range from 2 to 150, more preferably in the range from 5 to 100 and even more preferably in the range from 10 to 50, v and w in the radicals of formula (I') are 0 and the groups $R^2$—O— in the radicals of formula (I') are derived from alcohols selected from octanol, decanol, dodecanol, tetradecanol, hexadecanol, octadecanol, eicosanol, behenyl alcohol, fatty alcohols having C-chain cuts between 8 and 22, preferably $C_{10}/C_{12}$ fatty alcohol, $C_{12}/C_{14}$ fatty alcohol, $C_{12}/C_{15}$ fatty alcohol, $C_{16}/C_{18}$ fatty alcohol, branched fatty alcohols, preferably Guerbet alcohols, monounsaturated fatty alcohols, preferably delta-9-cis-hexadecanol, delta-9-cis-octadecanol, trans-9-octadecanol and cis-delta-11-octadecanol.

Particularly preferred phosphoric esters of formula (III) according to the present invention are those wherein the radicals of formula (I') are derived from $C_{16/18}$ fatty alcohol ethoxylates with 10-50 ethylene oxide units, preferably from substances selected from $C_{16/18}$ fatty alcohol ethoxylate with 11 ethylene oxide units, $C_{16/18}$ fatty alcohol ethoxylate with 25 ethylene oxide units and $C_{16/18}$ fatty alcohol ethoxylate with 50 ethylene oxide units.

Further particularly preferred phosphoric esters of formula (III) are those wherein the total number of the therein contained radicals of formula (I'), preferably the total number of the therein contained radicals of formula (I') where u is from 1 to 200, preferably from 2 to 150, more preferably from 5 to 100 and even more preferably from 10 to 50 and v and w are 0 is from 4 to 20, preferably from 4 to 10 and more preferably from 4 to 6.

Further preferred phosphoric esters of formula (III) are those wherein the total number of ethylene oxide units in the structural units of formulae (I') and (II') together per radical of formula (I') is from 30 to 100 and preferably from 40 to 80.

The present invention also provides mixtures comprising one or more phosphoric esters of the present invention. In one preferred embodiment of the present invention, these mixtures may also comprise phosphoric esters having just one phosphorus atom per molecule, in particular those of the formula

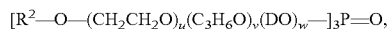

$[R^2-O-(CH_2CH_2O)_u(C_3H_6O)_v(DO)_w-]_3P=O$, where $R^2$, u, v, w and D are each as defined above under the compounds of formula (I). Among these mixtures, preference is in turn given to those which consist of the phosphoric esters mentioned. The proportion of the mixtures of the present invention which is attributable to the phosphoric esters of the present invention is preferably greater than 50% by weight, more preferably in the range from 70% to 100% by weight and even more preferably in the range from 80% to 100% by weight. In another preferred embodiment of the present invention, the mixtures of the present invention consist of the phosphoric esters of the present invention.

The phosphoric esters of the present invention are prepared by reacting phosphoric acid or derivatives thereof with alcohol, preferably fatty alcohol ethoxylate, and diol at temperatures of 150 to 250° C., preferably of 180 to 240° C. and more preferably of 200 to 230° C.

Suitable phosphoric acid derivatives are polyphosphoric acid, tetraphosphorus decaoxide, phosphoryl chloride and phosphorus pentachloride.

Orthophosphoric acid is the preferred reactant.

The esterification is preferably carried on such that essentially neutral phosphoric esters of the present invention are present. Preference is given to a degree of conversion >80%, i.e., more than 80% of all esterifiable functions of the phosphoric acid or phosphoric acid derivatives are esterified. A degree of conversion >90% is particularly preferred and >95% even more particularly preferred.

The remaining free valences on the phosphorus atom can be acid groups, but also counter ions selected from $Li^+$, $Na^+$, $K^+$, $Mg^{++}$, $Ca^{++}$, $Al^{+++}$, $NH_4^+$ and quaternary ammonium ions $[HNR^1R^2R^3]^+$, where $R^1$, $R^2$ and $R^3$ independently can be hydrogen, a linear or branched alkyl group having 1 to 22 carbon atoms, a linear or branched mono- or polyunsaturated alkenyl group having 2 to 22 carbon atoms, a linear monohydroxyalkyl group having 2 to 10 carbon atoms, preferably a monohydroxyethyl or monohydroxypropyl group, and also a linear or branched dihydroxyalkyl group having 3 to 10 carbon atoms.

The degree of neutralization of the unsubstituted phosphorus valences (P—OH) can be between 0% and 100%.

Particularly preferred phosphoric esters of the present invention are obtainable from the reaction of a) 3-10 mol and preferably 4-8 mol of a $C_{12}$-$C_{22}$ fatty alcohol ethoxylate, preferably of a $C_{16/18}$ fatty alcohol ethoxylate, with 10-50 ethylene oxide units,
b) 2 mol of polyethylene glycol having an average molecular weight of 1500-8000, and
c) 2-5 mol and preferably 2.5-4 mol of orthophosphoric acid.

Especially preferred phosphoric esters of the present invention are obtainable from the reaction of a) 5 mol of a $C_{12}$-$C_{22}$ fatty alcohol ethoxylate, preferably of a $C_{16/18}$ fatty alcohol ethoxylate, with 10-50 ethylene oxide units, preferably 25 ethylene oxide units,
b) 2 mol of polyethylene glycol having an average molecular weight of 1500-8000, preferably having an average molecular weight of 4000, and
c) 3 mol of orthophosphoric acid.

Extremely preferred phosphoric esters of the present invention are obtainable from the reaction of a) 5 mol of a $C_{16/18}$ fatty alcohol ethoxylate with 25 ethylene oxide units,
b) 2 mol of polyethylene glycol having an average molecular weight of 4000, and
c) 3 mol of orthophosphoric acid.

The phosphoric esters of the present invention have excellent thickening capacity not only for compositions on an aqueous or aqueous-alcoholic basis but also for compositions on an aqueous-surfactant basis and tolerate even organic solvents such as alcohols.

The phosphoric esters of the present invention are also very useful as thickener, consistency regulator, emulsifier, sensory additive, solubilizer, dispersant, glidant, adhesive and stabilizer.

The present invention therefore also provides for the use of one or more of the phosphoric esters of the present invention as thickener, consistency regulator, emulsifier, sensory additive, solubilizer, dispersant, glidant, adhesive and stabilizer.

The phosphoric esters of the present invention are further very useful in the manufacture of cosmetic, pharmaceutical and dermatological compositions.

The phosphoric esters of the present invention are also very useful for thickening cosmetic, pharmaceutical and dermatological compositions comprising one or more surfactants. Shampoos are preferably concerned here.

The present invention therefore also provides for the use of one or more phosphoric esters of the present invention for thickening cosmetic, pharmaceutical and dermatological compositions comprising one or more surfactants, preferably for thickening shampoos.

It is particularly in deodorant or antiperspirant formulations comprising aluminum salts, preferably aluminum chlorohydrate or aluminum-zirconium complex salts, that the phosphoric esters of the present invention that are included therein reduce the formation of white residues on clothing donned after application of the formulations to the skin.

The present invention therefore also provides for the use of one or more phosphoric esters of the present invention in deodorant or antiperspirant formulations, in particular in deodorant or antiperspirant formulations comprising aluminum salts, preferably aluminum chlorohydrate or aluminum-zirconium complex salts, for reducing the formation of white residues on the clothing after using the deodorant or antiperspirant formulations on the skin.

The present invention further provides cosmetic, pharmaceutical and dermatological compositions comprising one or more of the phosphoric esters of the present invention.

The phosphoric esters of the present invention have manifold possible uses and are suitable for use in aqueous, aqueous-alcoholic and aqueous-surfactant compositions, emulsions, suspensions, dispersions, powders and sprays.

Preferred compositions of the present invention are present in the form of aqueous, aqueous-alcoholic or aqueous-surfactant compositions, emulsions, suspensions, dispersions, powders or sprays.

The phosphoric esters of the present invention can be used as thickeners for compositions on an aqueous or aqueous-alcoholic basis, for example hair gels, moisturizing gels, antiperspirant gels, bleaching gels, conditioners and disinfection gels. The phosphoric esters of the present invention are further useful as stabilizer, dispersant and consistency regulator for aqueous-surfactant preparations, for example shampoos, shower baths, shower gels and foam baths and for improving skin mildness and skin compatibility.

The thickening effect of the phosphoric esters of the present invention in aqueous-surfactant compositions is brought about by the association of the hydrophobic end groups with the surfactant micelles, and can be controlled through the choice of the ethoxylate end groups of the phosphoric esters of the present invention and through the choice of the surfactants.

The suspending/dispersing and stabilizing effect of the phosphoric esters of the present invention in aqueous-surfactant compositions is due to the association of the hydrophobic end groups and of the liquid components, for example oils and silicone oils, that are insoluble in aqueous-surfactant compositions, or of the insoluble solids components, for example pigments and active ingredients such as zinc pyrethiones.

The phosphoric esters of the present invention are similarly useful as thickeners and dispersants, as emulsifiers, suspending agents having a thickening effect and consistency regulators for emulsions and suspensions, such as conditioners, and also as glidant, adhesive, thickener, dispersing and emulsifying agents of decorative, solids-containing preparations. Mixtures of the phosphoric esters of the present invention can also be used. The emulsifying, stabilizing and/or consistency-regulating effect of the phosphoric esters of the present invention in emulsions is caused and enhanced, respectively, by an association between the hydrophobic end groups and also by an interaction of the hydrophobic end groups with the hydrophobic oil components.

In one preferred embodiment of the present invention, the cosmetic, pharmaceutical or dermatological compositions of the present invention are present as emulsions.

The emulsions can be not only water-in-oil emulsions but also oil-in-water emulsions, microemulsions and multiple emulsions.

The emulsions can be prepared in a known manner, i.e., for example, by hot, hot/cold or PIT emulsification.

The nonaqueous portion of the emulsions, which is largely made up of the emulsifier, the thickener and the oil body, is typically in the range from 5% to 95% by weight, preferably in the range from 15% to 75% by weight. It follows that the emulsions can comprise 5% to 95% by weight and preferably 25% to 85% by weight of water, depending on whether lotions having a comparatively low viscosity or creams and ointments of high viscosity are to be produced.

In a further preferred embodiment of the present invention, the phosphoric esters of the present invention are used in rinse-off products, preferably shampoos, shower baths, shower gels and foam baths.

In a further preferred embodiment of the present invention, the phosphoric esters of the present invention are used in leave-on products, preferably skincare agents such as day creams, night creams, moisturizing lotions and gels, aqueous gels, for example facial toners, care creams, nutrient creams, body lotions, ointments, sunscreen compositions, lip care compositions, antiperspirants and deodorants.

They are further also useful for surfactant-free aqueous compositions and emulsions and also for hair treatments, hair rinses and hair gels, but also for permanent wave compositions, hair colorants, and also for decorative cosmetics, for example make-ups, eye shadows, lipsticks, mascara and the like.

It is particularly advantageous that the thickening capacity is also marked in a strong acidic medium and in electrolyte-containing compositions.

The phosphoric esters of the present invention are therefore particularly useful for thickening and stabilizing acidic cosmetic compositions. These can be for example cosmetic compositions comprising hydroxyacids, such as lactic acid, glycolic acid, salicylic acid, citric acid or polyglycol diacids in free or partial neutralization. It is further possible to stabilize formulations comprising vitamin C or vitamin C derivatives, dihydroxyacetone or skin-whitening actives such as arbutin or glycyrrhetic acid and salts thereof.

In a further preferred embodiment of the present invention, the compositions of the present invention have a pH in the range from 2 to 10, preferably in the range from 2 to 6, more preferably in the range from 2.5 to 5 and even more preferably in the range from 3 to 4.5.

Particular preference is given to compositions of the present invention with a pH from 2.5 to 5 which, in addition to the phosphoric esters of the present invention and based on the entire composition, comprise from 0.05% to 3.0% by weight, preferably from 0.05% to 2.0% by weight and more preferably from 0.1% to 1.0% by weight of one or more organic acids having an antimicrobial effect, preferably carboxylic acids having an antimicrobial effect. Particularly preferred organic acids having an antimicrobial effect are benzoic acid, sorbic acid, salicylic acid, lactic acid and anissic acid. These acids can also be used in the compositions of the present invention, preferably in a cosmetic formulation, in the form of their sodium or potassium salts when the pH of the composition is later adjusted to a pH in the range from 2.5 to 5. In the process, the free, antimicrobially active acid is released. These compositions are particularly preferred because the phosphoric esters of the present invention, unlike the carboxylic esters of the prior art, provide in this pH range a longterm-stable thickening effect which makes the use of antimicrobially active acids as preservatives possible in the first place. This makes it possible to avoid other preservatives where skin reactions are more likely, examples being halogenated preservatives.

The individual organic acids having an antimicrobial effect, preferably the carboxylic acids having an antimicrobial effect, are preferably used in the just-described compositions of the present invention in an amount of 0.05% to 2.0% by weight and more preferably in an amount of 0.1% to 1.0% by weight, based on the entire composition.

The compositions of the present invention preferably comprise water, particularly preferably in an amount of 5% to 95% by weight. In one particularly preferred embodiment, they comprise 25% to 85% by weight of water. In another particularly preferred embodiment, they comprise 50% to 95% by weight, preferably 75% to 95% by weight of water.

The phosphoric esters of the present invention are also very useful as thickeners of electrolyte-containing compositions.

The electrolytes used are inorganic salts, preferably ammonium or metal salts, more preferably of halides, for example $CaCl_2$, $MgCl_2$, LiCl, KCl, NaCl, carbonates, bicarbonates, phosphates, sulfates, nitrates, more preferably sodium chloride, and/or organic salts, preferably ammonium or metal salts, more preferably of glycolic acid, lactic acid, citric acid, tartaric acid, mandelic acid, salicylic acid, ascorbic acid, pyruvic acid, fumaric acid, retinoic acid, sulfonic acids, benzoic acid, kojic acid, fruit acid, malic acid, gluconic acid and galacturonic acid.

As electrolyte, the compositions of the present invention may also comprise mixtures of various salts.

In a further preferred embodiment of the present invention, the compositions of the present invention comprise one or more electrolytes.

These include aqueous antiperspirant formulations comprising aluminum salts, preferably aluminum chlorohydrate or aluminum-zirconium complex salts.

The content of the one or more electrolytes in the compositions of the present invention is, based on the entire composition of the present invention, preferably in the range from 0.1% to 20.0% by weight, more preferably in the range from 0.2% to 10.0% by weight and even more preferably in the range from 0.5% to 5.0% by weight.

It is very advantageous that the phosphoric esters of the present invention both thicken and stabilize compositions comprising oxidizing agents, preferably hydrogen peroxide, for example hair colorants.

In a further preferred embodiment of the present invention, the compositions of the present invention comprise hydrogen peroxide or hydrogen peroxide releasers. These compositions are preferably present in the form of gels.

Useful hydrogen peroxide releasers preferably include inorganic peracids, preferably peroxosulfuric acid, peroxodisulfuric acid, peroxocarbonates, and also organic peracids, preferably peracetic acid.

In a further preferred embodiment of the present invention, the compositions of the present invention are acidic hydrogen peroxide bleaching gels or creams.

The compositions of the present invention comprise, based on the final cosmetic, pharmaceutical or dermatological compositions, preferably from 0.01% to 10.0% by weight, more preferably from 0.1% to 6.0% by weight and even more preferably from 0.5% to 3.0% by weight of the phosphoric esters of the present invention.

The compositions of the present invention may comprise anionic, cationic, nonionic, ampholytic surfactants and/or betaine surfactants.

The total amount of the surfactants used in the compositions of the present invention (in the case of rinse-off products for example) is, based on the final compositions of the present invention, preferably in the range from 1% to 70% by weight, more preferably in the range from 5% to 40% by weight and even more preferably in the range from 10% to 35% by weight.

The anionic surfactants are preferably ($C_{10}$-$C_{22}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic acid half-esters and diesters, fatty alcohol phosphates, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulforicinoleates, acyl glutamates and acyl glycinates. These compounds and mixtures thereof are used in the form of their water-soluble or water-dispersible salts, for example the sodium, potassium, magnesium, ammonium, mono-, di- and triethanolammonium, and analogous alkylammonium salts.

The amount of anionic surfactants in the compositions according to the invention is preferably from 2 to 30% by weight, particularly preferably from 5 to 25% by weight and especially preferably from 12 to 22% by weight, based on the final compositions.

Preferred cationic surfactants are quaternary ammonium salts, such as di($C_8$-$C_{22}$)-alkyldimethylammonium chloride or bromide, preferably di($C_8$-$C_{22}$)-alkyldimethylammonium chloride or bromide; ($C_8$-$C_{22}$)-alkyldimethylethylammonium chloride or bromide; ($C_8$-$C_{22}$)-alkyltrimethylammonium chloride or bromide, preferably cetyltrimethylammonium chloride or bromide and ($C_8$-$C_{22}$)-alkyltrimethylammonium chloride or bromide; ($C_{10}$-$C_{24}$)-alkyldimethylbenzylammonium chloride or bromide, preferably ($C_{12}$-$C_{18}$)-alkyldimethylbenzylammonium chloride, ($C_8$-$C_{22}$)-alkyldimethylhydroxyethylammonium chloride, phosphate, sulfate, lactate, ($C_8$-$C_{22}$)-alkylamidopropyltrimethylammonium chloride, methosulfate, N,N-bis(2-$C_8$-$C_{22}$-alkanoyloxyethyl)dimethylammonium chloride, methosulfate, N,N-bis(2-$C_8$-$C_{22}$-alkanoyloxyethyhydroxyethylmethylammonium chloride, methosulfate.

The amount of cationic surfactants in the compositions according to the invention is preferably 0.1 to 10% by weight, particularly preferably 0.5 to 7% by weight and especially preferably 1 to 5% by weight, based on the final compositions.

Preferred nonionic surfactants are fatty alcohol ethoxylates (alkylpolyethylene glycols); alkylphenol polyethylene glycols; fatty amine ethoxylates (alkylaminopolyethylene glycols); fatty acid ethoxylates (acyl polyethylene glycols); polypropylene glycol ethoxylates (Pluronics®); fatty acid alkanolamides (fatty acid amide polyethylene glycols); sucrose esters; sorbitol esters and sorbitan esters and polyglycol ethers thereof, and also $C_8$-$C_{22}$-alkyl polyglucosides.

The amount of nonionic surfactants in the compositions according to the invention (e.g. in the case of rinse-off products) is preferably in the range from 1 to 20% by weight, particularly preferably from 2 to 10% by weight and especially preferably from 3 to 7% by weight, based on the final compositions.

Furthermore, the compositions according to the invention can comprise amphoteric surfactants. These can be described as derivatives of long-chain secondary or tertiary amines which have an alkyl group with 8 to 18 carbon atoms and in which a further group is substituted by an anionic group which imparts the solubility in water, thus, for example, by a carboxyl, sulfate or sulfonate group. Preferred amphoteric surfactants are N—($C_{12}$-$C_{18}$)-alkyl-β-aminopropionates and N—($C_{12}$-$C_{18}$)-alkyl-β-iminodipropionates as alkali metal and mono-, di- and trialkylammonium salts; suitable further surfactants are also amine oxides. These are oxides of tertiary amines with a long-chain group having 8 to 18 carbon atoms and two mostly short-chain alkyl groups having 1 to 4 carbon atoms. Preference is given here, for example, to the $C_{10}$- to $C_{18}$-alkyldimethylamine oxides, fatty acid amidoalkyldimethylamine oxide.

A further preferred group of surfactants is betaine surfactants, also called zwitterionic surfactants. These contain in the same molecule a cationic group, in particular an ammonium group and an anionic group, which may be a carboxylate group, sulfate group or sulfonate group. Suitable betaines are preferably alkylbetaines such as cocobetaine or fatty acid alkylamidopropylbetaines, for example cocoacylamidopropyldimethylbetaine or the $C_{12}$- to $C_{18}$-dimethylaminohexanoates and/or the $C_{10}$- to $C_{18}$-acylamidopropanedimethylbetaines.

The amount of amphoteric surfactants and/or betaine surfactants in the compositions according to the invention is preferably from 0.5 to 20% by weight and particularly preferably from 1 to 10% by weight, based on the final compositions.

Preferred surfactants are lauryl sulfate, laureth sulfate, cocoamidopropylbetaine, alkylbetaines such as cocobetaine, sodium cocoyl glutamate and lauroamphoacetate.

In a further preferred embodiment of the invention, the compositions according to the invention additionally also comprise, as foam-boosting agents, cosurfactants from the group of alkylbetaines, alkylamidobetaines, aminopropionates, aminoglycinates, imidazolinium betaines and sulfobetaines, amine oxides, fatty acid alkanolamides and polyhydroxyamides.

In a preferred embodiment of the invention, the cosmetic, pharmaceutical or dermatological compositions and comprise, in addition to the one or more phosphoric esters according to the present invention, one or more surfactants.

The compositions according to the invention can comprise, as further auxiliaries and additives, oil bodies, silicone oils, waxes, emulsifiers, coemulsifiers, solubilizers, stabilizers, cationic polymers, film formers, thickeners, gelling agents, superfatting agents, refatting agents, antimicrobial active ingredients, biogenic active ingredients, astringents, deodorizing agents, sun protection filters, antioxidants, humectants, solvents, dyes, fragrances, pearlizing agents, opacifiers and/or water-soluble silicones.

The oil bodies can advantageously be selected from the groups of triglycerides, natural and synthetic fatty substances, preferably esters of fatty acids with alcohols of low carbon number, e.g. with isopropanol, propylene glycol or glycerol, or esters of fatty alcohols with alkanoic acids of low carbon number or with fatty acids or from the group of alkyl benzoates, and also natural or synthetic hydrocarbon oils.

Triglycerides of linear or branched, saturated or unsaturated, optionally hydroxylated, $C_8$-$C_{30}$-fatty acids, in particular vegetable oils, such as sunflower oil, corn oil, soybean oil, rice oil, jojoba oil, babusscu oil, pumpkin oil, grapeseed oil, sesame oil, walnut oil, apricot oil, orange oil, wheatgerm oil, peach kernel oil, macadamia oil, avocado oil, sweet almond oil, lady's smock oil, castor oil, olive oil, peanut oil, rapeseed oil and coconut oil, and also synthetic triglyceride oils, e.g. the commercial product Myritol® 318, are suitable. Hydrogenated triglycerides are also preferred according to the present invention. Oils of animal origin, for example beef tallow, perhydrosqualene, lanolin, can also be used A further class of oil bodies preferred according to the present invention is the benzoic acid esters of linear or branched $C_{8-22}$-alkanols, e.g. the commercial products Finsolv® SB (isostearyl benzoate), Finsolv® TN ($C_{12}$-$C_{15}$-alkyl benzoate) and Finsolv® EB (ethylhexyl benzoate).

A further class of oil bodies preferred according to the present invention is the dialkyl ethers having in total 12 to 36 carbon atoms, in particular having 12 to 24 carbon atoms, such as, for example, di-n-octyl ether (Cetiol® OE), di-n-nonyl ether, di-n-decyl ether, di-n-undecyl ether, di-n-dodecyl ether, n-hexyl n-octyl ether, n-octyl n-decyl ether, n-decyl n-undecyl ether, n-undecyl n-dodecyl ether and n-hexyl n-undecyl ether, di-3-ethyldecyl ether, tert-butyl n-octyl ether, isopentyl n-octyl ether and 2-methylpentyl n-octyl ether, and di-tert-butyl ether and diisopentyl ether.

Branched saturated or unsaturated fatty alcohols having 6-30 carbon atoms, e.g. isostearyl alcohol, and Guerbet alcohols, are likewise suitable.

A further class of oil bodies preferred according to the present invention is hydroxycarboxylic acid alkyl esters. Preferred hydroxycarboxylic acid alkyl esters are full esters of glycolic acid, lactic acid, malic acid, tartaric acid or citric acid. Further esters of hydroxycarboxylic acids which are suitable in principle are esters of β-hydroxypropionic acid, of tartronic acid, of D-gluconic acid, sugar acid, mucic acid or glucuronic acid. Suitable alcohol components of these esters are primary, linear or branched aliphatic alcohols having 8 to 22 carbon atoms. Here, the esters of $C_{12}$-$C_{15}$-fatty alcohols are particularly preferred. Esters of this type are commercially available, e.g. under the trade name Cosmacol® from EniChem, Augusta Industriale.

A further class of oil bodies preferred according to the present invention is dicarboxylic acid esters of linear or branched $C_2$-$C_{10}$-alkanols, such as di-n-butyl adipate (Cetiol® B), di(2-ethylhexyl) adipate and di(2-ethylhexyl) succinate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate, and also diisotridecyl azelate.

Likewise preferred oil bodies are symmetrical, asymmetrical or cyclic esters of carbonic acid with fatty alcohols, glycerol carbonate or dicaprylyl carbonate (Cetiol® CC).

A further class of oil bodies preferred according to the present invention is the esters of dimers of unsaturated $C_{12}$-$C_{22}$-fatty acids (dimer fatty acids) with monovalent linear, branched or cyclic $C_2$-$C_{18}$-alkanols or with polyvalent linear or branched $C_2$-$C_6$-alkanols.

A further class of oil bodies preferred according to the present invention is hydrocarbon oils, for example those with linear or branched, saturated or unsaturated $C_7$-$C_{40}$-carbon chains, for example Vaseline, dodecane, isododecane, cholesterol, lanolin, synthetic hydrocarbons such as polyolefins, in particular polyisobutene, hydrogenated polyisobutene, polydecane, and hexadecane, isohexadecane, paraffin oils, isoparaffin oils, e.g. the commercial products of the Permethyl® series, squalane, squalene, and alicyclic hydrocarbons, e.g. the commercial product 1,3-di(2-ethylhexyl)cyclohexane (Cetiol® S), ozokerite, and ceresine.

Silicone oils and silicone waxes which are available are preferably dimethylpolysiloxanes and cyclomethicones, polydialkylsiloxanes $R_3SiO(R_2SiO)_xSiR_3$, where R is methyl or ethyl, particularly preferably methyl, and x is a number from 2 to 500, for example the dimethicones available under the trade names VICASIL (General Electric Company), DOW CORNING 200, DOW CORNING 225, DOW CORNING 200 (Dow Corning Corporation), and also the dimethicones available under SilCare® Silicone 41M65, SilCare® Silicone 41M70, SilCare® Silicone 41M80 (Clariant), stearyldimethylpolysiloxane, $C_{20}$-$C_{24}$-alkyldimethylpolysiloxane, $C_{24}$-$C_{28}$-alkyldimethylpolysiloxane, but also the methicones available under SilCare® Silicone 41M40, SilCare® Silicone 41M50 (Clariant), furthermore trimethylsiloxysilicates $[(CH_2)_3SiO)_{1/2}]_x[SiO_2]_y$, where x is a number from 1 to 500 and y is a number from 1 to 500, dimethiconols $R_3SiO[R_2SiO]_xSiR_2OH$ and $HOR_2SiO[R_2SiO]_xSiR_2OH$, where R is methyl or ethyl and x is a number up to 500, polyalkylarylsiloxanes, for example the polymethylphenylsiloxanes available under the trade names SF 1075 METHYLPHENYL FLUID (General Electric Company) and 556 COSMETIC GRADE PHENYL TRIMETHICONE FLUID (Dow Corning Corporation), polydiarylsiloxanes, silicone resins, cyclic silicones and amino-, fatty-acid-, alcohol-, polyether-, epoxy-, fluorine- and/or alkyl-modified silicone compounds, and also polyether siloxane copolymers.

The compositions according to the invention can comprise waxes, for example paraffin waxes, microwaxes and ozokerites, beeswax and its part fractions, and also beeswax derivatives, waxes from the group of homopolymeric polyethylenes or copolymers of α-olefins, and natural waxes such as rice wax, candelilla wax, carnauba wax, Japan wax or shellac wax.

Emulsifiers, coemulsifiers and solubilizers which can be used are nonionic, anionic, cationic or amphoteric surface-active compounds.

Suitable nonionogenic surface-active compounds are preferably:
addition products of from 0 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group and onto sorbitan or sorbitol esters; ($C_{12}$-$C_{18}$)-fatty acid mono- and diesters of addition products of from 0 to 30 mol of ethylene oxide onto glycerol; glycerol mono- and diesters and sorbitan mono- and diesters of saturated and unsaturated fatty acids having 6 to 22 carbon atoms and optionally ethylene oxide addition products thereof; addition products of from 15 to 60 mol of ethylene oxide onto castor oil and/or hydrogenated castor oil; polyol and in particular polyglycerol esters, such as, for example, polyglycerol polyricinoleate and polyglycerol poly-12-hydroxystearate. Ethoxylated fatty amines, fatty acid amides, fatty acid alkanolamides and mixtures of compounds of two or more of these substance classes are likewise preferably suitable.

Suitable ionogenic coemulsifiers are, for example, anionic emulsifiers, such as mono-, di- or triphosphoric acid esters, soaps (e.g. sodium stearate), fatty alcohol sulfates, but also cationic emulsifiers such as mono-, di- and trialkyl quats and polymeric derivatives thereof.

Available amphoteric emulsifiers are preferably alkylaminoalkylcarboxylic acids, betaines, sulfobetaines and imidazoline derivatives.

Fatty alcohol ethoxylates selected from the group of ethoxylated stearyl alcohols, isostearyl alcohols, cetyl alcohols, isocetyl alcohols, oleyl alcohols, lauryl alcohols, isolauryl alcohols, cetylstearyl alcohols, in particular polyethylene glycol(13) stearyl ether, polyethylene glycol(14) stearyl ether, polyethylene glycol(15) stearyl ether, polyethylene glycol(16) stearyl ether, polyethylene glycol(17) stearyl ether, polyethylene glycol(18) stearyl ether, polyethylene glycol(19) stearyl ether, polyethylene glycol(20) stearyl ether, polyethylene glycol(12) isostearyl ether, polyethylene glycol(13) isostearyl ether, polyethylene glycol(14) isostearyl ether, polyethylene glycol(15) isostearyl ether, polyethylene glycol(16) isostearyl ether, polyethylene glycol(17) isostearyl ether, polyethylene glycol(18) isostearyl ether, polyethylene glycol(19) isostearyl ether, polyethylene glycol(20) isostearyl ether, polyethylene glycol(13) cetyl ether, polyethylene glycol(14) cetyl ether, polyethylene glycol(15) cetyl ether, polyethylene glycol(16) cetyl ether, polyethylene glycol(17) cetyl ether, polyethylene glycol(18) cetyl ether, polyethylene glycol(19) cetyl ether, polyethylene glycol(20) cetyl ether, polyethylene glycol(13) isocetyl ether, polyethylene glycol(14) isocetyl ether, polyethylene glycol(15) isocetyl ether, polyethylene glycol(16) isocetyl ether, polyethylene glycol(17) isocetyl ether, polyethylene glycol(18) isocetyl ether, polyethylene glycol(19) isocetyl ether, polyethylene glycol(20) isocetyl ether, polyethylene glycol(12) oleyl ether, polyethylene glycol(13) oleyl ether, polyethylene glycol(14) oleyl ether, polyethylene glycol(15) oleyl ether, polyethylene glycol(12) lauryl ether, polyethylene glycol(12) isolauryl ether, polyethylene glycol(13) cetylstearyl ether, polyethylene glycol(14) cetylstearyl ether, polyethylene glycol(15) cetylstearyl ether, polyethylene glycol(16) cetylstearyl ether, polyethylene glycol(17) cetylstearyl ether, polyethylene glycol(18) cetylstearyl ether, polyethylene glycol(19) cetylstearyl ether are particularly preferably used.

Fatty acid ethoxylates selected from the group of ethoxylated stearates, isostearates and oleates, in particular polyethylene glycol(20) stearate, polyethylene glycol(21) stearate, polyethylene glycol(22) stearate, polyethylene glycol(23) stearate, polyethylene glycol(24) stearate, polyethylene glycol(25) stearate, polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol(21) isostearate, polyethylene glycol(22) isostearate, polyethylene glycol(23) isostearate, polyethylene glycol (24) isostearate, polyethylene glycol(25) isostearate, polyethylene glycol(12) oleate, polyethylene glycol(13) oleate, polyethylene glycol(14) oleate, polyethylene glycol(15) oleate, polyethylene glycol(16) oleate, polyethylene glycol (17) oleate, polyethylene glycol(18) oleate, polyethylene glycol(19) oleate, polyethylene glycol(20)oleate are likewise preferred.

Sodium laureth-11 carboxylate can advantageously be used as ethoxylated alkylether carboxylic acid or salts thereof.

Ethoxylated triglycerides which can be used are advantageously polyethylene glycol(60) evening primrose glycerides.

It is furthermore advantageous to select the polyethylene glycol glycerol fatty acid esters from the group polyethylene glycol(20) glyceryl laurate, polyethylene glycol(6) glyceryl caprate/caprinate, polyethylene glycol(20) glyceryl oleate, polyethylene glycol(20) glyceryl isostearate and polyethylene glycol(18) glyceryl oleate/cocoate.

Among the sorbitan esters, polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate are particularly suitable.

Particularly advantageous coemulsifiers are glyceryl monostearate, glyceryl monooleate, diglyceryl monostearate, glyceryl isostearate, polyglyceryl-3 oleate, polyglyceryl-3 diisostearate, polyglyceryl-4 isostearate, polyglyceryl-2 dipolyhydroxystearate, polyglyceryl-4 dipolyhydroxystearate, PEG-30 dipolyhydroxystearate, diisostearoyl polyglyceryl-3 diisostearate, glycol distearate and polyglyceryl-3 dipolyhydroxystearate, sorbitan monoisostearate, sorbitan stearate, sorbitan oleate, sucrose distearate, lecithin, PEG-7-hydrogenated castor oil, cetyl alcohol, stearyl alcohol, behenyl alcohol, isobehenyl alcohol and polyethylene glycol(2) stearyl ether (steareth-2), alkylmethicone copolyols and alkyldimethicone copolyols, in particular cetyldimethicone copolyol, laurylmethicone copolyol.

The compositions according to the invention can comprise one or more of the emulsifiers, coemulsifiers or solubilizers in amounts of from 0.1 to 20% by weight, preferably 1 to 15% by weight and particularly preferably 3 to 10% by weight, based on the final compositions.

Stabilizers which can be used are metal salts of fatty acids, such as, for example, magnesium stearate, aluminum stearate and/or zinc stearate, preferably in amounts of from 0.1 to 10% by weight, preferably 0.5 to 8% by weight and particularly preferably 1 to 5% by weight, based on the final compositions.

Suitable cationic polymers are those known under the INCI name "Polyquaternium", in particular Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and Polyquaternium 37&mineral oil&PPG trideceth (Salcare SC95), PVP-dimethylaminoethyl methacrylate copolymer, guar hydroxypropyltriammonium chlorides, and calcium alginate and ammonium alginate. Furthermore, cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as, for example, amidomethicones; copolymers of adipic acid and dimethylaminohydroxypropyldiethylenetriamine; polyaminopolyamide and cationic chitin derivatives, such as, for example, chitosan, can be used.

The compositions according to the invention can comprise one or more of the aforementioned cationic polymers in amounts of from 0.1 to 5% by weight, preferably 0.2 to 3% by weight and particularly preferably 0.5 to 2% by weight, based on the final compositions.

Furthermore, the compositions according to the invention can comprise film formers which, depending on the intended use, are selected from salts of phenylbenzimidazolesulfonic acid, water-soluble polyurethanes, for example $C_{10}$-polycarbamyl polyglyceryl ester, polyvinyl alcohol, water-soluble acrylic acid polymers/copolymers and esters or salts thereof, for example partial ester copolymers of acrylic acid/methacrylic acid, water-soluble cellulose, for example hydroxymethylcellulose, hydroxyethylcellulose, hydroxypropylcellulose, water-soluble quaterniums, polyquaterniums, carboxyvinyl polymers, such as carbomers and salts thereof, polysaccharides, for example polydextrose and glucan, vinyl acetate/crotonate, for example available under the trade name Aristoflex® A 60 (Clariant).

The compositions according to the invention can comprise one or more film formers in amounts of from 0.1 to 10% by weight, preferably from 0.2 to 5% by weight and particularly preferably from 0.5 to 3% by weight, based on the final compositions.

The desired viscosity of the compositions can be established by adding thickeners and gelling agents. Of suitability are preferably cellulose ethers and other cellulose derivatives (e.g. carboxymethylcellulose, hydroxyethylcellulose), gelatin, starch and starch derivatives, sodium alginates, fatty acid polyethylene glycol esters, agar, tragacanth or dextrin derivatives, in particular dextrin esters. Furthermore, metal salts of fatty acids, preferably having 12 to 22 carbon atoms, for example sodium stearate, sodium palmitate, sodium laurate, sodium arachidates, sodium behenate, potassium stearate, potassium palmitate, sodium myristate, aluminum monostearate, hydroxy fatty acids, for example 12-hydroxystearic acid, 16-hydroxyhexadecanoyl acid; fatty acid amides; fatty acid alkanolamides; dibenzalsorbitol and alcohol-soluble polyamides and polyacrylamides or mixtures of such are suitable. Furthermore, crosslinked and uncrosslinked polyacrylates such as carbomers, sodium polyacrylates or polymers containing sulfonic acid, such as ammonium acryloyldimethyltaurate/VP copolymer, can be used.

Preferably, the compositions according to the invention comprise 0.01 to 20% by weight, particularly preferably 0.1 to 10% by weight, especially preferably 0.2 to 3% by weight and very particularly preferably 0.4 to 2% by weight, of thickeners and/or gelling agents.

Superfatting agents which can be used are preferably lanolin and lecithin, nonethoxylated and polyethoxylated or acylated lanolin derivatives and lecithin derivatives, polyol fatty acid esters, mono-, di- and triglycerides and/or fatty acid alkanolamides, where the latter simultaneously serve as foam stabilizers, which are preferably used in amounts of from 0.01 to 10% by weight, particularly preferably from 0.1 to 5% by weight and especially preferably from 0.5 to 3% by weight, based on the final compositions according to the invention.

The antimicrobial active ingredients used are cetyltrimethylammonium chloride, cetylpyridinium chloride, benzethonium chloride, diisobutylethoxyethyldimethylbenzylammonium chloride, sodium N-laurylsarcosinate, sodium N-palmethylsarcosinate, lauroylsarcosine, N-myristoylglycine, potassium N-laurylsarcosine, trimethylammonium chloride, sodium aluminum chlorohydroxylactate, triethyl citrate, tricetylmethylammonium chloride, 2,4,4'-trichloro-2'-hydroxydiphenyl ether (triclosan), phenoxyethanol, 1,5-pentanediol, 1,6-hexanediol, 3,4,4'-trichlorocarbanilide (triclocarban), diaminoalkylamide, for example L-lysine hexadecylamide, citrate heavy metal salts, salicylates, piroctoses, in particular zinc salts, pyrithiones and heavy metal salts thereof, in particular zinc pyrithione, zinc phenol sulfate, farnesol, ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, selenium disulfide and Octopirox®, iodopropynyl butylcarbamate, methylchloroisothiazolinone, methylisothiazolinone, methyldibromoglutaronitrile, AgCl, chloroxylenol, Na salt of diethylhexyl sulfosuccinate, sodium benzoate, and phenoxyethanol, benzyl alcohol, phenoxyisopropanol, parabens, preferably butyl, ethyl, methyl and propyl paraben, and Na salts thereof, pentanediol, 1,2-octanediol, 2-bromo-2-nitropropane-1,3-diol, ethylhexylglycerol, benzyl alcohol, sorbic acid, benzoic acid, lactic acid, imidazolidinylurea, diazolidinylurea, dimethyloldimethylhydantoin (DMDMH), Na salt of hydroxymethylglycinate, hydroxyethylglycine of sorbic acid and combinations of these active substances.

The compositions according to the invention comprise the antimicrobial active ingredients preferably in amounts of from 0.001 to 5% by weight, particularly preferably from 0.01 to 3% by weight and especially preferably from 0.1 to 2% by weight, based on the final compositions.

The compositions according to the invention can furthermore comprise biogenic active ingredients selected from plant extracts, such as, for example, aloe vera, and also local anesthetics, antibiotics, antiphlogistics, antiallergics, corticosteroids, sebostatics, Bisabolol®, allantoin, Phytantriol®, proteins, vitamins selected from niacin, biotin, vitamin B2, vitamin B3, vitamin B6, vitamin B3 derivatives (salts, acids, esters, amides, alcohols), vitamin C and vitamin C derivatives (salts, acids, esters, amides, alcohols), preferably as sodium salt of the monophosphoric acid ester of ascorbic acid or as magnesium salt of the phosphoric acid ester of ascorbic acid, tocopherol and tocopherol acetate, and also vitamin E and/or derivatives thereof.

The compositions according to the invention can comprise biogenic active ingredients preferably in amounts of from 0.001 to 5% by weight, particularly preferably from 0.01 to 3% by weight and especially preferably from 0.1 to 2% by weight, based on the final compositions.

The compositions according to the invention can comprise astringents, preferably magnesium oxide, aluminum oxide, titanium dioxide, zirconium dioxide and zinc oxide, oxide hydrates, preferably aluminum oxide hydrate (boehmite) and hydroxides, preferably of calcium, magnesium, aluminum, titanium, zirconium or zinc, and also aluminum chlorohydrates, preferably in amounts of from 0 to 50% by weight, particularly preferably in amounts of from 0.01 to 10% by weight and especially preferably in amounts of from 0.1 to 10% by weight. Allantoin and bisabolol are preferred as deodorizing substances. These are preferably used in amounts of from 0.0001 to 10% by weight.

The compositions according to the invention can comprise microfine titanium dioxide, mica-titanium oxide, iron oxides, mica-iron oxide, zinc oxide, silicon oxides, ultramarine blue, chromium oxides as pigments/micropigments and also as sun protection filters.

The compositions according to the invention can comprise sun protection filters, preferably selected from 4-aminobenzoic acid, 3-(4'-trimethylammonium)benzylideneboran-2-one methyl sulfate, camphorbenzalkoniummethosulfate, 3,3,5-trimethylcyclohexyl salicylate, 2-hydroxy-4-methoxybenzophenone, 2-phenylbenzimidazole-5-sulfonic acid and its potassium, sodium and triethanolamine salts, 3,3'-(1,4-phenylenedimethine)bis(7,7-dimethyl-2-oxobicyclo[2.2.1]heptane-1-methanesulfonic acid) and its salts, 1-(4-tert-butylphenyl)-3-(4-methoxyphenyl)propane-1,3-dione, 3-(4'-sulfo)benzylidenebornan-2-one and its salts, 2-ethylhexyl 2-cyano-3,3-diphenylacrylate, polymers of N-[2(and 4)-(2-oxoborn-3-ylidenemethyl)benzyl]acrylamide, 2-ethylhexyl 4-methoxycinnamate, ethoxylated ethyl 4-aminobenzoate, isoamyl 4-methoxycinnamate, 2,4,6-tris[p-(2-ethylhexyloxycarbonyl)anilino]-1,3,5-triazine, 2-(2H-benzotriazol-2-yl)-4-methyl-6-(2-methyl-3-(1,3,3,3-tetramethyl-1-(trimethylsilyloxy)disiloxanyl)propyl)phenol, bis(2-ethylhexyl) 4,4'-[(6-[4-((1,1-dimethylethyl)aminocarbonyl)phenylamino]-1,3,5-triazin-2,4-yl)diimino]bisbenzoate, benzophenone-3, benzophenone-4 (acid), 3-(4'-methylbenzylidene)-D,L-camphor, 3-benzylidenecamphor, 2-ethylhexyl salicylate, 2-ethylhexyl 4-dimethylaminobenzoate, hydroxy-4-methoxybenzophenone-5-sulfonic acid (sulfisobenzone) and the sodium salt, 4-isopropylbenzyl salicylate, N,N,N-trimethyl-4-(2-oxoborn-3-ylidenemethyl) anilium methyl sulfate, homosalate (INN), oxybenzone (INN), 2-phenylbenzimidazole-5-sulfonic acid and its sodium, potassium and triethanolamine salts, octylmethoxycinnamic acid, isopentyl-4-methoxycinnamic acid, isoamyl-p-methoxycinnamic acid, 2,4,6-trianilino(p-carbo-2'-ethylhexyl-1'-oxy)-1,3,5-triazine (octyltriazone) phenol, 2-2(2H-benzotriazol-2-yl)-4-methyl-6-(2-methyl-3-(1,3,3,3-tetramethyl-1-(trimethylsily)oxy)disiloxanyl)propyl (drometrizoletrisiloxane) benzoic acid, 4,4-((6-(((1,1-dimethylethyl)amino)carbonyl)phenyl)amino)-1,3,5-triazine-2,4-diyl)diimino)bis,bis(2-ethylhexyl)ester)benzoic acid, 4,4-((6-(((1,1-dimethylethy)amino)carbonyl)phenyl)amino)-1,3,5-triazine-2,4-diyl)diimino)bis,bis(2-ethylhexy)ester), 3-(4'-methylbenzylidene)-D,L-camphor (4-methylbenzylidenecamphor), benzylidenecamphorsulfonic acid, octocrylene, polyacrylamidomethylbenzylidenecamphor, 2-ethylhexyl salicylate (octylsalicylate), ethyl-2-hexyl 4-dimethylaminobenzoate (octyldimethyl PABA), PEG-25 PABA, 2-hydroxy-4-methoxybenzophenone-5-sulfonic acid (benzophenone-5) and the Na salt, 2,2'-methylenebis-6-(2H-benzotriazol-2-yl)-4-(tetramethylbutyl)-1,1,3,3-phenol, sodium salt of 2-2'-bis(1,4-phenylene)-1H-benzimidazole-4,6-disulfonic acid, (1,3,5)-triazine-2,4-bis((4-(2-ethylhexyloxy)-2-hydroxy)phenyl)-6-(4-methoxyphenyl), 2-ethylhexyl 2-cyano-3,3-diphenyl-2-propenoate, glyceryl octanoate, di-p-methoxycinnamic acid, p-aminobenzoic acid and esters thereof, 4-tert-butyl-4'-methoxydibenzoylmethane, 4-(2-β-glucopyranoxy)propoxy-2-hydroxybenzophenone, octyl salicylate, methyl-2,5-diisopropylcinnamic acid, cinoxate, dihydroxydimethoxybenzophenone, disodium salt of 2,2'-dihydroxy-4,4'-dimethoxy-5,5'-disulfobenzophenone, dihydroxybenzophenone, 1,3,4-dimethoxyphenyl-4,4-dimethyl-1,3-pentanedione, 2-ethylhexyl dimethoxybenzylidenedioxoimidazolidinepropionate, methylenebisbenzotriazolyl tetramethylbutylphenol, phenyl dibenzimidazoletetrasulfonate, bis-ethylhexyloxyphenol methoxyphenol triazine, tetrahydroxybenzophenones, terephthalylidenedicamphorsulfonic acid, 2,4,6-tris[4,2-ethylhexyloxycarbonyl)anilino]-1,3,5-triazine, methylbis(trimethylsiloxy)silylisopentyltrimethoxycinnamic acid, amyl p-dimethylaminobenzoate, amyl p-dimethylaminobenzoate, 2-ethylhexyl p-dimethylaminobenzoate, isopropyl-p-methoxycinnamic acid/diisopropylcinnamic acid esters, 2-ethylhexyl-p-methoxycinnamic acid, 2-hydroxy-4-methoxybenzophenone, 2-hydroxy-4-methoxybenzophenone-5-sulfonic acid and the trihydrate, and also 2-hydroxy-4-methoxybenzophenone-5-sulfonate sodium salt and phenylbenzimidazolesulfonic acid.

The amount of the aforementioned sun protection filters (one or more compounds) in the compositions is preferably 0.001 to 30% by weight, particularly preferably 0.05 to 20% by weight and especially 1 to 10% by weight, based on the total weight of the final composition.

The compositions according to the invention can comprise antioxidants, preferably selected from amino acids (e.g. glycine, histidine, tyrosine, tryptophan) and derivatives thereof, imidazoles (e.g. urocanic acid) and derivatives thereof, peptides such as DL-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof), and also salts thereof, dilauryl thiodipropionate, distearyl thiodipropionate, thiodipropionic acid and derivatives thereof (e.g. esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses, also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, trans-stilbene oxide), superoxide dismutase and the derivatives suitable according to the invention (salts, esters, ethers, sugars, nucleotides, nucleosides, peptides and lipids) of these specified substances.

The antioxidants can protect the skin and the hair against oxidative stress. Preferred antioxidants here are vitamin E and derivatives thereof, and vitamin A and derivatives thereof.

The amount of the one or more antioxidants in the compositions according to the invention is preferably 0.001 to 30% by weight, particularly preferably 0.05 to 20% by weight and especially preferably 1 to 10% by weight, based on the total weight of the composition.

Furthermore, humectants selected from the sodium salt of 2-pyrrolidone-5-carboxylate (NaPCA), guanidine; glycolic acid and salts thereof, lactic acid and salts thereof, glucosamines and salts thereof, lactamide monoethanolamine, acetamide monoethanolamine, urea, hydroxy acids, panthenol and derivatives thereof, for example D-panthenol (R-2,4-dihydroxy-N-(3-hydroxypropyl)-3,3-dimethylbutamide), DL-panthenol, calcium pantothenate, panthetine, pantotheine, panthenyl ethyl ether, isopropyl palmitate, glycerol and/or sorbitol can be used, preferably in amounts of from 0.1 to 15% by weight and particularly preferably from 0.5 to 5% by weight, based on the final compositions.

Additionally, the compositions according to the invention can comprise organic solvents. In principle, suitable organic solvents are all mono- or polyhydric alcohols. Preference is given to using alcohols having 1 to 4 carbon atoms, such as ethanol, propanol, isopropanol, n-butanol, isobutanol, t-butanol, glycerol and mixtures of said alcohols. Further preferred alcohols are polyethylene glycols with a relative molecular mass below 2000. In particular, a use of polyethylene glycol with a relative molecular mass between 200 and 600 and in amounts up to 45% by weight and of polyethylene glycol with a relative molecular mass between 400 and 600 in amounts of from 5 to 25% by weight is preferred. Further suitable solvents are, for example, triacetin (glycerol triacetate) and 1-methoxy-2-propanol.

The dyes and color pigments present in the compositions according to the invention, both organic and inorganic dyes, are selected from the corresponding positive list of the Cosmetics Regulations or the EU list of cosmetic colorants.

| Chemical or other name | CIN | Color |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Cerise Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfonic acid diethylamide-1'-phenylazo)-3-hydroxy-5''-chloro-2'',4''-dimethoxy-2-naphthoic acid anilide | 12490 | red |
| Disperse Yellow 16 | 12700 | yellow |
| 1-(4-Sulfo-1-phenylazo)-4-aminobenzenesulfonic acid | 13015 | yellow |
| 2,4-Dihydroxyazobenzene-4'-sulfonic acid | 14270 | orange |
| 2-(2,4-Dimethylphenylazo-5-sulfonic acid)-1-hydroxy-naphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonic acid-4-chloro-5-carboxylic acid-1-phenylazo)-2-hydroxynaphthalene | 15525 | red |
| 1-(3-Methylphenylazo-4-sulfonic acid)-2-hydroxynaphthalene | 15580 | red |
| 1-(4',(8')-Sulfonic acid naphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthylcarboxylic acid | 15800 | red |
| 1-(2-Sulfo-4-methyl-1-phenylazo)-2-naphthylcarboxylic acid | 15850 | red |
| 1-(2-Sulfo-4-methyl-5-chloro-1-phenylazo)-2-hydroxy-naphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-((4'-Sulfo-2'',4''-dimethyl)bisphenylazo)-1,3-dihydroxy-benzene | 20170 | orange |
| Acid Black 1 | 20470 | black |
| Pigment Yellow 13 | 21100 | yellow |

-continued

| Chemical or other name | CIN | Color |
|---|---|---|
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4'-[(4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-Carotenealdehyde ($C_{30}$) | 40820 | orange |
| trans-Apo-8'-Carotenic acid ($C_{30}$)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenyl-carbinol | 42051 | blue |
| 4-[(4-N-Ethyl-p-sulfobenzylamino)phenyl(4-hydroxy-2-sulfophenyl)(methylene)-1-(N-ethyl-N-p-sulfobenzyl)-2,5-cyclohexadieneimine] | 42053 | green |
| Acid Blue 7 | 42080 | blue |
| (N-Ethyl-p-sulfobenzylaminophenyl(2-sulfophenyl)-methylene(N-ethyl-N-p-sulfobenzyl)cyclohexadieneimine | 42090 | blue |
| Acid Green 9 | 42100 | green |
| Diethyldisulfobenzyldi-4-amino-2-chlorodi-2-methyl-fuchsonimmonium | 42170 | green |
| Basic Violet 14 | 42510 | violet |
| Basic Violet 2 | 42520 | violet |
| 2'-Methyl-4'-(N-ethyl-N-m-sulfobenzyl)amino-4''-(N-diethyl)-amino-2-methyl-N-ethyl-N-m-sulfobenzylfuchsonimmonium | 42735 | blue |
| 4'-(N-Dimethyl)amino-4''-(N-phenyl)aminonaphtho-N-dimethylfuchsonimmonium | 44045 | blue |
| 2-Hydroxy-3,6-disulfo-4,4'-bisdimethylaminonaphtho-fuchsinimmonium | 44090 | green |
| Acid red | 45100 | red |
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidine)anthraquinone | 61570 | green |
| Acid Blue 80 | 61585 | blue |
| Acid Blue 62 | 62045 | blue |
| N,N'-Dihydro-1,2,1',2'-anthraquinoneazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha, beta- or gamma-Carotene | 75130 | orange |
| Keto- and/or hydroxyl derivatives of carotene | 75135 | yellow |
| Guanine or pearlescent agents | 75170 | white |

-continued

| Chemical or other name | CIN | Color |
|---|---|---|
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of the chlorophylls and chlorophyllines | 75810 | green |
| Aluminum | 77000 | white |
| Aluminum hydrate | 77002 | white |
| Water-containing aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |
| Chromic oxide | 77288 | green |
| Chromic oxide, water-containing | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxides and hydroxides | 77491 | red |
| Hydrated iron oxide | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7H_2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)isoalloxazine, lactoflavin | | yellow |
| Caramel | | brown |
| Capsanthin, Capsorubin | | orange |
| Betanine | | red |
| Benzopyrilium salts, anthocyanines | | red |
| Aluminum, zinc, magnesium and calcium stearate | | white |
| Bromothymol Blue | | blue |
| Bromocresol Green | | green |
| Acid Red 195 | | red |

Oil-soluble natural dyes, such as, for example, paprika extracts, β-carotene and cochineal are furthermore advantageous.

Also advantageously used are pearlescent pigments, e.g. pearl essence (guanine/hypoxanthine mixed crystals from fish scales) and mother of pearl (ground mussel shells), monocrystalline pearlescent pigments such as, for example, bismuth oxychloride (BiOCl), layer substrate pigments, e.g. mica/metal oxide, silver-white pearlescent pigments from $TiO_2$, interference pigments ($TiO_2$, variable layer thickness), color luster pigments ($Fe_2O_3$) and combination pigments ($TiO_2/Fe_2O_3$, $TiO_2/Cr_2O_3$, $TiO_2$/Prussian blue, $TiO_2$/carmine).

Effect pigments within the context of the present invention are understood as meaning pigments which due to their refraction properties produce special optical effects. Effect pigments impart to the treated surface (skin, hair, mucous membrane) luster or glitter effects or can visually conceal unevenness of the skin and skin wrinkles by means of diffuse light scattering. As a particular embodiment of the effect pigments, interference pigments are preferred. Particularly suitable effect pigments are, for example, mica particles which are coated with at least one metal oxide. Besides mica, a sheet silicate, silica gel and other $SiO_2$ modifications are also suitable as carriers. A metal oxide frequently used for coating is, for example, titanium oxide, to which, if desired, iron oxide can be admixed. By means of the size and shape (e.g. spherical, ellipsoidal, flat, even, uneven) of the pigment particles and by means of the thickness of the oxide coating, the reflection properties can be influenced. Other metal oxides, e.g. bismuth oxychloride (BiOCl), and the oxides of, for example, titanium, in particular the $TiO_2$ modifications anatase and rutile, aluminum, tantalum, niobium, zirconium and hafnium can also be used. Effect pigments can also be prepared using magnesium fluoride ($MgF_2$) and calcium fluoride (fluorspar, $CaF_2$).

The effects can be controlled both by means of the particle size and by means of the particle size distribution of the pigment ensemble. Suitable particle size distributions extend, for example, from 2-50 μm, 5-25 μm, 5-40 μm, 5-60 μm, 5-95 μm, 5-100 μm, 10-60 μm, 10-100 μm, 10-125 μm, 20-100 μm, 20-150 μm, and <15 μm. A wider particle size distribution, for example of 20-150 μm, produces glittering effects, whereas a narrower particle size distribution of <15 μm provides for a uniform silky appearance.

The compositions of the present invention comprise effect pigments preferably in amounts from 0.1% to 20% by weight, more preferably from 0.5% to 10% by weight and even more preferably from 1% to 5% by weight, all based on the total weight of the composition.

Preference as deodorizing substances is given to allantoin and bisabolol. These are preferably used in amounts from 0.0001% to 10% by weight.

Fragrance and/or perfume oils which may be used are individual odorant compounds, e.g. the synthetic products of the ester, ether, aldehyde, ketone, alcohol and hydrocarbon types. Odorant compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexyl propionate, styrallyl propionate and benzyl salicylate. The ethers include, for example, benzyl ethyl ethers, the aldehydes include, for example, the linear alkanals having 8 to 18 carbon atoms, citral, citronellal, citronellyloxyacetaldehyde, cyclamenaldehyde, hydroxycitronellal, lilial and bourgeonal, the ketones include, for example, the ionones, alpha-isomethylionone and methyl cedryl ketone, the alcohols include anethol, citronellol, eugenol, geraniol, linalool, phenylethyl alcohol and terpineol, and the hydrocarbons include primarily the terpenes and balsams. Preference is given to using mixtures of different odorants which together produce a pleasing scent note.

Perfume oils can also comprise natural odorant mixtures, as are accessible from vegetable or animal sources, e.g. pine oil, citrus oil, jasmine oil, lily oil, rose oil or ylang-ylang oil. Essential oils of relatively low volatility, which in most cases are used as aromatic components, are also suitable as perfume oils, e.g. sage oil, chamomile oil, clove oil, melissa oil, mint oil, cinnamon leaf oil, linden blossom oil, juniperberry oil, vetiver oil, olibanum oil, galbanum oil and ladanum oil.

Preferably suitable as pearlizing component are fatty acid monoalkanolamides, fatty acid dialkanolamides, monoesters or diesters of alkylene glycols, in particular ethylene glycol and/or propylene glycol or oligomers thereof, with higher fatty acids, such as, for example, palmitic acid, stearic acid and behenic acid, monoesters or polyesters of glycerol with carboxylic acids, fatty acids and metal salts thereof, ketosulfones or mixtures of the specified compounds. Particular preference is given to ethylene glycol distearates and/or polyethylene glycol distearates having on average 3 glycol units.

When the compositions according to the invention comprise pearlizing compounds, these are preferably present in the compositions according to the invention in an amount of from 0.1 to 15% by weight and particularly preferably in an amount of from 1 to 10% by weight.

The acids or alkalis used for adjusting the pH are preferably mineral acids, for example HCl, inorganic bases, for example NaOH or KOH, and organic acids, preferably citric acid.

The following examples and applications are intended to further elucidate the invention without, however, limiting it thereto. All percentages are percent (%) by weight.

PREPARATION EXAMPLES

General Operating Procedure

In the preparation of the phosphoric esters of the present invention, phosphoric acid (85% strength), diol and fatty alcohol ethoxylate are used in a certain molar ratio. For this purpose, all starting materials are initially charged in a stirred apparatus equipped with heating mantle, separator with condenser and vacuum connection. The mixture is heated to 100° C. and three times evacuated down to 100 mbar and subsequently refilled with nitrogen. After a further 4 hours of inertization (nitrogen being introduced at 20 liters/hour) at 100° C., the batch is heated to 230° C. while nitrogen is being introduced and esterified (water removed in the separator). The reaction times are 24 to 42 hours (reckoned from 230° C. esterification temperature), particularly 40 hours. The residual acid number is then <3 mg KOH/g. This corresponds approximately to 93 to 96% conversion (based on starting acid number). After the reaction has ended, the product is cooled to 80° C. and poured into a dish and the solidified melt is comminuted.

Example 1

Ester from 11.5 g of phosphoric acid, 197.5 g of polyglycol 4000 and 296.0 g of ceteareth-25 ($C_{16/18}$ fatty alcohol+25 mol of ethylene oxide) in a molar ratio of 2:1:4 (formula $E_2$), residual acid number: 1.5 mg KOH/g (96% conversion), $^{31}$P NMR: diester/triester=13/87 mol %.

Example 2

Ester from 13.8 g of phosphoric acid, 316.1 g of polyglycol 4000 and 296.0 g of ceteareth-25 ($C_{16/18}$ fatty alcohol+25 mol of ethylene oxide) in a molar ratio of 3:2:5 (formula $E_2M$), residual acid number: 1.9 mg KOH/g (94% conversion), $^{31}$P NMR: diester/triester=18/82 mol %.

Example 3

Ester from 15.4 g of phosphoric acid, 395.1 g of polyglycol 4000 and 293.3 g of ceteareth-25 ($C_{16/18}$ fatty alcohol+25 mol of ethylene oxide) in a molar ratio of 4:3:6 (formula $E_2M_2$ and $E_3V$), residual acid number: 2.3 mg KOH/g (93% conversion), $^{31}$P NMR: diester/triester=18/82 mol %.

Example 4

Ester from 47.8 g of phosphoric acid, 1716.8 g of polyglycol 6000 and 515.9 g of ceteareth-11 ($C_{16/18}$ fatty alcohol+11 mol of ethylene oxide) in a molar ratio of 3:2:5 (formula $E_2M_2$ and $E_3V$), residual acid number: 2.3 mg KOH/g (93% conversion), $^{31}$P NMR: diester/triester=20/80 mol %.

Example 5

Ester from 13.8 g of phosphoric acid, 117.5 g of polyglycol 1500 and 425.0 g of ceteareth-50 ($C_{16/18}$ fatty alcohol+50 mol of ethylene oxide) in a molar ratio of 3:2:5 (formula $E_2M_2$ and $E_3V$), residual acid number: 1.9 mg KOH/g (94% conversion), $^{31}$P NMR: diester/triester=16/84 mol %.

Example 6

Ester from 11.5 g of phosphoric acid, 73.4 g of polyglycol 1500 and 296.0 g of ceteareth-25 ($C_{16/18}$ fatty alcohol+25 mol of ethylene oxide) in a molar ratio of 2:1:4 (formula $E_2$), residual acid number: 2.5 mg KOH/g (94% conversion), $^{31}$P NMR: diester/triester=13/87 mol %.

Example 7

Ester from 11.5 g of phosphoric acid, 409.5 g of polyglycol 8000 and 296.0 g of ceteareth-25 ($C_{16/18}$ fatty alcohol+25 mol of ethylene oxide) in a molar ratio of 2:1:4 (formula $E_2$), residual acid number: 1.1 mg KOH/g (95% conversion), $^{31}$P NMR: diester/triester=13/87 mol %.

Example 8

Ester from 13.8 g of phosphoric acid, 117.4 g of polyglycol 1500 and 296.0 g of ceteareth-25 ($C_{16/18}$ fatty alcohol+25 mol of ethylene oxide) in a molar ratio of 3:2:5 (formula $E_2M_2$ and $E_3V$), residual acid number: 2.4 mg KOH/g (95% conversion), $^{31}P$ NMR: diester/triester=13/87 mol %.

Example 9

Ester from 13.8 g of phosphoric acid, 655.2 g of polyglycol 8000 and 296.0 g of ceteareth-25 ($C_{16/18}$ fatty alcohol+25 mol of ethylene oxide) in a molar ratio of 3:2:5 (formula $E_2M_2$ and $E_3V$), residual acid number: 1.0 mg KOH/g (95% conversion), $^{31}P$ NMR: diester/triester=11/89 mol %.

Example 10

Ester from 15.4 g of phosphoric acid, 146.8 g of polyglycol 1500 and 293.3 g of ceteareth-25 ($C_{16/18}$ fatty alcohol+25 mol of ethylene oxide) in a molar ratio of 4:3:6 (formula $E_2M_2$ and $E_3V$), residual acid number: 3.7 mg KOH/g (93% conversion), $^{31}P$ NMR: diester/triester=16/84 mol %.

Example 11

Ester from 15.4 g of phosphoric acid, 819.0 g of polyglycol 8000 and 293.3 g of ceteareth-25 ($C_{16/18}$ fatty alcohol+25 mol of ethylene oxide) in a molar ratio of 4:3:6 (formula $E_2M_2$ and $E_3V$), residual acid number: 1.4 mg KOH/g (93% conversion), $^{31}P$ NMR: diester/triester=19/81 mol %.

COMPARATIVE EXAMPLES

Comparative examples used were PEG 150 pentaerythrityl tetrastearate (Crothix), PEG 150 polyglyceryl 2-tristearate (Genapol® DAT 100) and PEG 150 distearate (Rewopal® PEG 6000 DS), typical ethoxylated fatty acid esters. The viscosity was measured at 20° C. with an RVT type Brookfield viscometer at 20 rpm immediately after preparation of the solutions to be measured ("Viscosity as-prepared") and after storage of the corresponding solutions.

TABLE 1

Viscosity of 6% by weight aqueous solutions of preparation Examples 1 to 11 compared with commercial products

| Product | Viscosity as-prepared [mPa · s] | Clarity | Viscosity after 3 months' storage at RT [mPa · s] |
|---|---|---|---|
| Example 1 | 76000 | clear | n.d. |
| Example 2 | 76000 | clear | 38200 |
| Example 3 | 67500 | clear | 34200 |
| Example 4 | 158000 | clear | n.d. |
| Example 5 | 103000 | clear | n.d. |
| Example 6 | 17600 | clear | n.d. |
| Example 7 | 47200 | clear | 41600 |
| Example 8 | 73000 | clear | n.d. |
| Example 9 | 36200 | clear | 29400 |
| Example 10 | 79000 | clear | 75500 |
| Example 11 | 13500 | clear | 10800 |
| PEG 150 pentaerythrityl tetrastearate | 6650 | slightly cloudy, precipitate | 990 |
| PEG 150 polyglyceryl 2-tristearate | 65 | cloudy, precipitate | n.d. |
| PEG 150 distearate | 3900 | cloudy | n.d. | n.d. not determined; RT: room temperature

It is apparent from Table 1 that the inventive phosphoric esters according to Examples 1 to 11 provide clear gels of high viscosity in water compared with the comparative examples; secondly, the viscosity reduction in storage is distinctly less than in the case of PEG 150 pentaerythrityl tetrastearate for example.

TABLE 2

Viscosity of 1% by weight solution in sodium laureth ether sulfate with 2 ethylene oxide units (INCI: Sodium Laureth Sulfate): Cocamidopropylbetaine 8:2, 15% by weight active substance Sodium Laureth Sulfate/Cocamidopropylbetaine, pH 4-4.4

| Product | Viscosity as-prepared [mPa · s] | Viscosity after 4 months' storage at 50° C. [mPa · s] |
|---|---|---|
| Example 1 | 79000 | 78000 |
| Example 2 | 45200 | 68000 |
| Example 8 | 38000 | n.d. |
| Example 10 | 47400 | 74000 |
| PEG 150 pentaerythrityl tetrastearate | 20000 | 80 |
| PEG 150 polyglyceryl 2-tristearate | 23100 | 110 |
| PEG 150 distearate | 2750 | 45 | n.d. not determined

It is apparent in Table 2 that the inventive phosphoric esters according to Examples 1, 2, 8 and 10 give gels of high viscosity in surfactant (compared with the comparative examples) which, unlike the comparative examples, do not lose viscosity in the course of storage.

FORMULATION EXAMPLES

Formulation Example 1

Facial Cleansing Foam

| A | stearic acid | 1.60% |
|---|---|---|
|   | myristic acid | 1.80% |
|   | lauric acid | 0.70% |
|   | Tegin M Glyceryl Stearate | 0.50% |
|   | palmitic acid | 0.70% |
| B | water | ad 100.00% |
| C | potassium hydroxide | 0.70% |
|   | phosphoric ester of Example 1 | 1.00% |

Preparation:

| I | Melt A at 80° C. |
| II | Dissolve C in B with stirring and at 60° C., then add to I. |
| III | Cool down with stirring. |

Formulation Example 2

Cream Rinse

| A | Genamin ® CTAC Cetrimonium Chloride | (Clariant) | 6.00% |
|---|---|---|---|
|   | Hostacerin ® DGL PEG-10 Diglyceryl-2 Laurate | (Clariant) | 1.50% |
|   | Cetylstearyl Alcohol |   | 1.70% |
|   | paraffin oil |   | 1.00% |
| B | water |   | ad 100.00% |
| C | phosphoric ester of Example 4 |   | 1.00% |
| D | perfume |   | 0.30% |
|   | panthenol |   | 0.30% |
|   | preservative |   | q.s. |
|   | dye |   | q.s. |

-continued

Preparation:

| | |
|---|---|
| I | Dissolve A at 75° C. |
| II | Dissolve C in B with stirring at 60° C. |
| III | Add II to I with stirring. Stir until cold. |
| IV | At 40° C. add the components of D. |
| V | Adjust the pH to 4. |

Formulation Example 3

Light Leave on for Hair Tips

| | | | |
|---|---|---|---|
| A | SilCare ® Silicone 41M15 | (Clariant) | 0.30% |
| | Caprylyl Methicone | | |
| B | Genapol ® LA 070 | (Clariant) | 8.00% |
| | Laureth-7 | | |
| C | water | | ad 100% |
| D | phosphoric ester of Example 2 | | 2.00% |
| E | Biobranil | | 0.50% |
| | Soybean (*Glycine Soja*) Oil and Wheat | | |
| | (*Triticum Vulgare*) Bran Lipids | | |
| | glycerol | | 2.00% |
| | panthenol | | 0.50% |
| F | SilCare ® Silicone SEA | (Clariant) | 0.50% |
| | Trideceth-9 PG Amodimethicone and | | |
| | Trideceth-12 | | |
| | Genamin ® CTAC | (Clariant) | 2.00% |
| | Cetrimonium Chloride | | |
| | Nipaguard ® DMDMH | (Clariant) | 0.20% |
| | DMDMH Hydantoin | | |

Preparation:

| | |
|---|---|
| I | Solubilize A in B. |
| II | Dissolve D in C with stirring at 60° C. |
| III | Add E to II and stir until the solution is clear, then add to I. |
| IV | Add F to III. |

Formulation Example 4

Hydrogen Peroxide Gel

| | | | |
|---|---|---|---|
| A | phosphoric ester of Example 3 | | 5.00% |
| | Genapol ® T 250 | (Clariant) | 2.00% |
| | Ceteareth-25 | | |
| B | water | | ad 100.00% |
| C | phosphoric acid | | 0.04% |
| | sodium dihydrogen phosphate | | 1.00% |
| D | hydrogen peroxide 30% strength | | 18.00% |

Preparation:

| | |
|---|---|
| I | Dissolve A in B with stirring and heating to 50° C. |
| II | Add C at 25° C. |
| III | Add D at room temperature. |

Formulation Example 5

Deodorant Gel

| | | | |
|---|---|---|---|
| A | Octopirox ® | (Clariant) | 0.10% |
| | Piroctone Olamine | | |
| B | Emulsogen ® HCP 049 | (Clariant) | 10.00% |
| | PEG-40 Hydrogenated Castor Oil and | | |
| | Propylene Glycol | | |
| | perfume | | 0.20% |
| C | water | | ad 100.00% |
| D | phosphoric ester of Example 5 | | 3.00% |
| E | citric acid | | q.s. |

Preparation:

| | |
|---|---|
| I | Dissolve A in B. |
| II | Dissolve D in C with stirring and slight heating, then add II to I. |
| III | If necessary, adjust the pH to 6.0 with E. |

Formulation Example 6

Make-Up Remover

| | | | |
|---|---|---|---|
| A | Velsan ® P8-3 | (Clariant) | 5.00% |
| | Isopropyl C12-15 | | |
| | Pareth-9 Carboxylate | | |
| B | Hostapon ® CGN | (Clariant) | 2.00% |
| | Sodium Cocoyl Glutamate | | |
| | Genagen ® CAB | (Clariant) | 3.00% |
| | Cocamidopropyl Betaine | | |
| | Allantoin | (Clariant) | 0.30% |
| | Aristoflex ® PEA | (Clariant) | 1.00% |
| | Polypropylene | | |
| | Terephthalate | | |
| | 1.6 Hexanediol | | 2.00% |
| | 1.2 Propanediol | | 2.00% |
| | Polyglycol 400 | (Clariant) | 2.00% |
| | PEG-8 | | |
| | panthenol | | 0.50% |
| | Lutrol F 127 | | 3.00% |
| | Poloxamer 407 | | |
| | preservative | | q.s. |
| C | phosphoric ester of Example 10 | | 1.00% |
| D | water | | ad 100.00% |
| E | Genapol ® LA 070 | (Clariant) | 2.00% |
| | Laureth-7 | | |

Preparation:

| | |
|---|---|
| I | A little at a time add the components of B to A and stir until a clear solution forms. |
| II | Dissolve C in D with stirring and slight heating, add II to I. |
| III | Stir E into I. |

Formulation Example 7

Whitening Gel

| | | |
|---|---|---|
| A | water | ad 100.00% |
| | arginine | 1.10% |
| | phosphoric ester of Example 11 | 4.00% |

-continued

| | | | |
|---|---|---|---|
| B | dipropylene glycol | | 8.00% |
| | Genapol ®C 100 Coceth-10 | (Clariant) | 0.60% |
| | Sodium citrate*2H₂O | | 0.09% |
| | citric acid 10.0% | | 0.10% |
| | Nipagin ® M Methylparaben | (Clariant) | 0.20% |
| | ascorbic acid 2-glucoside | | 2.00% |
| Preparation: | | | |

I Mix the components of A and dissolve with stirring and slight heating.
II Add the components of B to I and dissolve. If necessary, heat the formulation slightly.

Formulation Example 8

Facial Toner

| | | | |
|---|---|---|---|
| A | glycerol | | 8.00% |
| | Polyglycol 400 PEG-8 | (Clariant) | 5.00% |
| | panthenol | | 0.50% |
| | perfume | | 0.20% |
| | alcohol | | 8.00% |
| | preservative | | q.s. |
| | Allantoin | (Clariant) | 0.10% |
| | Niacinamide | | 0.10% |
| | Extrapon *Hamamelis* water, Witch Hazel Distillate, SD Alcohol 39-C, Butylene Glycols | | 1.00% |
| B | water | | ad 100% |
| C | phosphoric ester of Example 6 | | 2.00% |
| Preparation: | | | |

I Dissolve C in B with stirring and slight heating.
II Add the components of A to I and stir until formulation is homogeneous.

Formulation Example 9

Hair Shampoo

| | | | |
|---|---|---|---|
| A | Genapol ® LRO liquid Sodium Laureth Sulfate | (Clariant) | 30.00% |
| | Hostapon ® CGN Sodium Cocoyl Glutamate | (Clariant) | 5.00% |
| | perfume | | 0.30% |
| B | water | | ad 100.00% |
| C | phosphoric ester of Example 7 | | 1.50% |
| | preservative | | q.s. |
| | dye | | q.s. |
| | Genagen ® CAB Cocamidopropyl Betaine | (Clariant) | 8.00% |
| Preparation: | | | |

I Dissolve C in B with stirring and heating to 50° C.
II A little at a time stir the components of A into I.
III If necessary, adjust the pH.

Formulation Example 10

Foam Bath

| | | | |
|---|---|---|---|
| A | Genapol ® LRO liquid Sodium Laureth Sulfate | (Clariant) | 60.00% |
| B | Medialan ® LD Sodium Lauroyl Sarcosinate | (Clariant) | 8.00% |
| | perfume | | 1.50% |
| | Velsan ® CG 070 PEG-7 Glyceryl Cocoate | (Clariant) | 5.00% |
| C | phosphoric ester of Example 2 | | 1.00% |
| D | water | | ad 100% |
| E | dye | | q.s. |
| | preservative | | q.s. |
| | Genagen ® CAB Cocamidopropyl Betaine | (Clariant) | 6.00% |
| Preparation: | | | |

I A little at a time stir the components of B into A.
II Dissolve C in D with stirring and heating to 50° C.
III Add I to II.
VI Stir E into III.
V If necessary, adjust the pH.

Formulation Example 11

O/W Skin Milk

| | | | |
|---|---|---|---|
| A | Hostacerin ® DGI Polyglyceryl-2 Sesqui-isostearate | (Clariant) | 2.00% |
| | Isopropyl palmitate | | 4.00% |
| | Octyldodecanol | | 4.00% |
| | Nipaguard ® PDU Propylene Glycol (and) Diazolidinyl Urea (and) Methylparaben (and) Propylparaben | (Clariant) | q.s. |
| B | Aristoflex ® AVC Ammonium Acryloyldimethyltaurate/ VP Copolymer | (Clariant) | 1.20% |
| C | Hostapon ® CGN Sodium Cocoyl Glutamate | (Clariant) | 0.60% |
| | water | | ad 100% |
| D | phosphoric ester of Example 2 | | 1.00% |
| E | perfume | | 0.40% |
| Preparation: | | | |

I Dissolve D in C with stirring and heating to 50° C.
II Add B to A, then add I and stir thoroughly.
III Add E to II.
IV Finally homogenize the formulation.

Formulation Example 12

Antiperspirant Roll-on

| | | | |
|---|---|---|---|
| A | phosphoric ester of Example 2 | | 1.50% |
| B | water | | ad 100.00% |
| C | Locron ® L Aluminum Chlorohydrate | (Clariant) | 20.00% |

-continued

| | | | |
|---|---|---|---|
| D | Genapol ® T 250<br>Ceteareth-25 | (Clariant) | 5.00% |
| | Butylene Glycol | | 3.00% |
| | Cetiol OE<br>Dicaprylyl Ether | | 1.00% |
| | Glyceryl Isostearate | | 2.00% |
| E | SilCare ® Silicone SEA<br>Trideceth-9 PG Amodimethicone and<br>Trideceth-12 | (Clariant) | 0.50% |

Preparation:

I  Dissolve A in B with stirring and heating to 60° C.
II  Add C to I.
III  Melt D at 50° C. and add II and stir until a clear solution has formed.
IV  Add E at 30° C.

Formulation Example 12 displayed a distinct reduction of white residues on the clothing after use of the roll-on on the skin compared with the same formulation but without phosphoric ester according to Example 2.

Formulation Example 13

Vitamin C Gel

| | | | |
|---|---|---|---|
| A | phosphoric ester of Example 2 | | 1.00% |
| | Genapol ® T 250<br>Ceteareth-25 | (Clariant) | 2.00% |
| B | water | | ad 100.00% |
| C | ascorbic acid | | 3.00% |
| D | Aristoflex AVC<br>Ammonium Acryloyldimethyltaurate/<br>VP Copolymer | (Clariant) | 0.80% |

Preparation:

I  Dissolve A in B with stirring at 50° C.
II  Stir C into I at room temperature.
III  Add D and stir until a homogeneous gel has formed.

Formulation Example 14

Shower Bath

| | | | |
|---|---|---|---|
| A | phosphoric ester of Example 2 | (Clariant) | 3.00% |
| | Aristoflex ® PEA<br>Polypropylene-Terephthalate | (Clariant) | 2.00% |
| B | water | | ad 100% |
| C | Genapol ® LRO liquid<br>Sodium Laureth Sulfate | (Clariant) | 30.00% |
| | Genapol ® LA 030<br>Laureth-3 | (Clariant) | 1.50% |
| | Hostapon ® CLG<br>Sodium Lauroyl Glutamate | (Clariant) | 5.00% |
| | Genagen ® KB<br>Coco Betaine | (Clariant) | 6.00% |
| | perfume | | 0.30% |
| | dye | | q.s. |
| | preservative | | q.s. |

Preparation:

I  Dissolve A in B at 50° C.
II  Stir the components of C into I in succession.
III  Adjust pH if necessary.

Formulation Example 15

Facial Anti-Aging Cream Gel

| | | | |
|---|---|---|---|
| A | phosphoric ester of Example 8 | (Clariant) | 1.00% |
| B | water | | ad 100.00% |
| C | paraffin oil | | 5.00% |
| | SilCare ® Silicone 31M50<br>Caprylyl Trimethicone | (Clariant) | 3.00% |
| D | Aristoflex ® AVC<br>Ammonium Acryloyldimethyl-<br>taurate/VP Copolymer | (Clariant) | 1.80% |
| E | glycolic acid 30% * | | 6.00% |
| | Phenonip ®<br>Phenoxyethanol (and) Methylparaben<br>(and) Ethylparaben (and) Butyl-<br>paraben (and) Propylparaben<br>(and) Isobutylparaben | (Clariant) | 0.50% |
| F | Genapol ® LA 070<br>Laureth-7 | (Clariant) | 2.00% |

Preparation:

I  Dissolve A in B with stirring at 50° C.
II  Stir D into C.
III  Stir I into II and stir until a homogeneous gel has formed.
IV  Add E into III.
V  Stir F into IV and stir until cream gel is homogeneous.

* neutralized to pH 4 with NaOH.

Formulation Example 16

O/W Self-tanning Cream

| | | | |
|---|---|---|---|
| A | Hostaphat ® CC 100<br>Cetyl Phosphate | (Clariant) | 1.0% |
| | Glyceryl Stearate | | 0.5% |
| | Cetearyl Alcohol | | 0.5% |
| | paraffin oil | | 8.0% |
| | isopropyl palmitate | | 7.0% |
| | SilCare ® Silicone 41M15<br>Caprylyl Methicone | (Clariant) | 1.0% |
| B | Aristoflex ® AVC<br>Ammonium Acryloyldimethyltaurate/<br>VP Copolymer | (Clariant) | 1.2% |
| C | water | | ad 100% |
| D | phosphoric ester of Example 9 | (Clariant) | 1.0% |
| E | Hostapon ® CLG<br>Sodium Lauroyl Glutamate | (Clariant) | 0.5% |
| | glycerol | | 5.0% |
| F | Tocopheryl Acetate | | 1.0% |
| | Fragrance | | 0.2% |
| | Preservative | | q.s. |
| G | Dihydroxyacetone | | 5.0% |
| H | water | | 8.0% |
| I | sodium hydroxide (10% in water) | | q.s. |

Preparation:

I  Melt A at 80° C.
II  Stir B into A.
III  Dissolve D in C at 50° C., then add E.
IV  Stir III into II.
V  Add F at room temperature.
VI  Dissolve G in H and stir into V.
VII  Adjust pH to 4-5 with I if necessary.

Formulation Example 17

O/W Sunscreen Milk

| | | | |
|---|---|---|---|
| A | Hostaphat ® CK 100 | (Clariant) | 2.00% |
| | Potassium Cetyl Phosphate | | |
| | SilCare ® Silicone 41M15 | (Clariant) | 1.00% |
| | Caprylyl Methicone | | |
| | stearic acid | | 0.50% |
| | Cetyl Alcohol | | 0.50% |
| | Cutina ® GMS | | 1.00% |
| | Glyceryl Stearate | | |
| | Cetiol ® SN | | 4.00% |
| | Cetearyl Isononanoate | | |
| | Velsan ® CCT | (Clariant) | 4.00% |
| | Caprylic/Capric Triglyceride | | |
| | Neo ® Heliopan BB | | 1.50% |
| | Benzophenone - 3 | | |
| | Eusolex ® 6300 | | 4.00% |
| | 4-Methylbenzylidene Camphor | | |
| B | Aristoflex ® AVC | (Clariant) | 0.40% |
| | Ammonium Acryloyldimethyltaurate/ | | |
| | VP Copolymer | | |
| C | water | | ad 100% |
| D | phosphoric ester of Example 2 | (Clariant) | 1.00% |
| E | glycerol | | 3.00% |
| | Eusolex ® 232 | | 2.00% |
| | Phenylbenzimidazole Sulfonic Acid | | |
| | Tris(hydroxymethyl)aminomethane | | 1.10% |
| | Tromethamine | | |
| F | Tocopheryl Acetate | | 0.50% |
| | Phenonip ® | (Clariant) | 0.50% |
| | Phenoxyethanol (and) Methylparaben | | |
| | (and) Butylparaben (and) Ethylparaben | | |
| | (and) Propylparaben | | |
| | Fragrance | | 0.40% |
| | Preparation: | | |

I   Melt A at 80° C., then add B.
II  Dissolve D in C at 60° C.
III Stir E into II.
IV  Dissolve III in I.
V   Add F into IV at 35° C.

Formulation Example 18

Facial Anti-Aging Gel

| | | | |
|---|---|---|---|
| A | Genapol ® T 250 | (Clariant) | 1.00% |
| | Ceteareth-25 | | |
| | phosphoric ester of Example 2 | (Clariant) | 1.00% |
| B | water | | ad 100% |
| C | Aristoflex ® AVC | (Clariant) | 2.00% |
| | Ammonium Acryloyldimethyltaurate/ | | |
| | VP Copolymer | | |
| D | Glycolic acid 30%* | | 6.00% |
| | Phenonip ® | (Clariant) | 0.50% |
| | Phenoxyethanol (and) Methylparaben | | |
| | (and) Ethylparaben (and) Butylparaben | | |
| | (and) Propylparaben (and) Isobutylparaben | | |
| | Preparation: | | |

I   Dissolve A in B with stirring at 50° C.
II  Add C and stir until a homogeneous gel has formed.
III Add D and stir until the gel is again homogeneous.

*neutralized to pH 4 with NaOH.

Formulation Example 19

Hair Shampoo

| | | | |
|---|---|---|---|
| A | Genapol ® LRO liquid | (Clariant) | 30.00% |
| | Sodium Laureth Sulfate | | |
| | Hostapon ® CGN | (Clariant) | 5.00% |
| | Sodium Cocoyl Glutamate | | |
| | perfume | | 0.30% |
| B | water | | ad 100.00% |
| C | phosphoric ester of Example 7 | | 1.50% |
| | benzoic acid | | 0.50% |
| | dye | | q.s. |
| | Genagen ® CAB | (Clariant) | 8.00% |
| | Cocamidopropyl Betaine | | |
| | Preparation: | | |

I   Dissolve C in B with stirring and heating to 50° C.
II  A little at a time stir the components of A into I.
III Adjust the pH to 4.6.

Formulation Example 20

Foam Bath

| | | | |
|---|---|---|---|
| A | Genapol ® LRO liquid | (Clariant) | 60.00% |
| | Sodium Laureth Sulfate | | |
| B | Medialan ® LD | (Clariant) | 8.00% |
| | Sodium Lauroyl Sarcosinate | | |
| | perfume | | 1.50% |
| | Velsan ® CG 070 | (Clariant) | 5.00% |
| | PEG-7 Glyceryl Cocoate | | |
| C | phosphoric ester of Example 2 | | 1.00% |
| D | water | | ad 100% |
| E | dye | | q.s. |
| | sorbic acid | | 0.40% |
| | Genagen ® CAB | (Clariant) | 6.00% |
| | Cocamidopropyl Betaine | | |
| | Preparation: | | |

I   A little at a time stir the components of B into A.
II  Dissolve C in D with stirring and heating to 50° C.
III Add I to II.
IV  Stir E into III.
V   Adjust the pH to 4.9.

Formulation Example 21

Shower Bath

| | | | |
|---|---|---|---|
| A | phosphoric ester of Example 2 | (Clariant) | 3.00% |
| | Aristoflex ® PEA | (Clariant) | 2.00% |
| | Polypropylene Terephthalate | | |
| B | water | | ad 100% |
| C | Genapol ® LRO liquid | (Clariant) | 30.00% |
| | Sodium Laureth Sulfate | | |
| | Genapol ® LA 030 | (Clariant) | 1.50% |
| | Laureth-3 | | |
| | Hostapon ® CLG | (Clariant) | 5.00% |
| | Sodium Lauroyl Glutamate | | |

-continued

| | | |
|---|---|---|
| Genagen ® KB | (Clariant) | 6.00% |
| Coco Betaine | | |
| perfume | | 0.30% |
| dye | | q.s. |
| sodium salicylate | | 0.50% |
| Preparation: | | |

I   Dissolve A in B at 50° C.
II  Stir the components of C into I in succession.
III Adjust the pH to 4.8.

The invention claimed is:
1. A phosphoric ester consisting of
A) at least one structural unit derived from substances of component a), the substances of component a) being selected from orthophosphoric acid and at least one compound selected from the group consisting of polyphosphoric acid, tetraphosphorus decaoxide, phosphoryl chloride and phosphorus pentachloride,
B) at least one structural unit derived from substances of component b), the substances of component b) being selected from at least one compound of formula (I)

$$R^2-O-(CH_2CH_2O)_u(C_3H_6O)_v(DO)_w-H \quad (I)$$

where
$R^2$ is a linear or branched, saturated alkyl group having 6 to 30, or is a linear or branched mono- or polyunsaturated alkenyl group having 6 to 30,
D is a linear or branched saturated alkylene group having 4 to 20 carbon atoms, is a linear or branched mono- or polyunsaturated alkenylene group having 4 to 20 carbon atoms or is $CH(aryl)CH_2-$,
u is a number from 0 to 200,
v is a number from 0 to 100,
w is a number from 0 to 100, and
where the groups $CH_2CH_2O$, $C_3H_6O$ and DO from the compounds of formula (I) can be arranged blocklike or randomly distributed, and
C) at least one structural unit derived from substances of component c), the substances of component c) being selected from at least one diol of formula (II)

$$HO-(CH_2CH_2O)_a(C_3H_6O)_b(DO)_c-H \quad (II)$$

where
D is as defined in formula (I),
a is a number from 0 to 800,
b is a number from 0 to 100,
c is a number from 0 to 100,
where the sum total a+b+c is ≥1, and the groups $CH_2CH_2O$, $C_3H_6O$ and DO from the compounds of formula (II) can be arranged blocklike or randomly distributed, and
the phosphoric ester contains 2 or more phosphorus atoms per molecule which are bridged via a structural unit derived from the compounds of formula (II).
2. A phosphoric ester according to claim 1 wherein at least 80%, of the maximum number of esterifiable functions theoretically obtainable from the substances of component a) are in an esterified state.
3. A phosphoric ester according to claim 1 wherein v and w in the structural units derived from the compounds of formula (I) are 0.
4. A phosphoric ester according to claim 1, wherein u in the structural units derived from the compounds of formula (I) is from 1 to 150.
5. A phosphoric ester according to claim 1, wherein b and c in the structural units derived from the compounds of formula (II) are 0.
6. A phosphoric ester according to claim 1, wherein a in the structural units derived from the compounds of formula (II) is from 10 to 200.
7. A phosphoric ester according to claim 1, wherein the at least one structural unit derived from the at least one diol of formula (II) is derived from diols selected from the group consisting of ethylene glycol, diethylene glycol, triethylene glycol, tetraethylene glycol, polyethylene glycol (PEG) having molecular weights from 200 to 35 000, preferably PEG 200, PEG 300, PEG 400, PEG 600, PEG 800, PEG 1000, PEG 1500, PEG 2000, PEG 3000, PEG 3350, PEG 4000, PEG 6000, PEG 8000, propylene glycol, dipropylene glycol, tripropylene glycol, polypropylene glycol, polybutylene glycol, copolymers of ethylene oxide and propylene oxide having molecular weights of 200 to 35 000, 1,2 butanediol, 1,3-butanediol, 1,4 butanediol, 1,2-pentanediol, 1,3-pentanediol, 1,4 pentanediol, 1,5-pentanediol, 1,2 hexanediol, 1,3-hexanediol, 1,4-hexanediol, 1,5 hexanediol, 1,6-hexanediol and 1,12-dodecanediol.
8. A phosphoric ester according to claim 1, wherein the at least one structural unit derived from the at least one compound of formula (I) are structural units wherein u is a number from 1 to 200, v and w are 0 and the radical $R^2O-$ is derived from alcohols selected from the group consisting of octanol, decanol, dodecanol, tetradecanol, hexadecanol, octadecanol, eicosanol, behenyl alcohol, fatty alcohols having C-chain cuts between 8 and 22, branched fatty alcohols, and monounsaturated fatty alcohols.
9. A phosphoric ester according to claim 1, wherein the total number of the structural units in the phosphoric ester which are derived from the at least one compound of formula (I), is in the range from 4 to 20.
10. A phosphoric ester according to claim 1, wherein the total number in the phosphoric ester of ethylene oxide units in the structural units derived from the substances of component b) and the substances of component c) is together in the range from 30 to 100 per fatty alcohol end group emerged from the compounds of formula (I).
11. A phosphoric ester according to claim 1, wherein the structural units derived from the substances of component a) are selected from structural units of formulae (A1) to (A3)

(A1)

(A2)

(A3)

where
M in each occurrence independently is H+ or a counter ion and the counter ions are selected from the group consisting of Li+, Na+, K+, Mg++, Ca++, Al+++, NH4+ and quaternary ammonium ions $[HNR^1R^2R^3]+$, where $R^1$, $R^2$ and $R^3$ independently can be hydrogen, a linear or branched alkyl group having 1 to 22 carbon atoms, a linear or branched mono- or polyunsaturated alkenyl group having 2 to 22 carbon atoms, a linear monohydroxyalkyl group having 2 to 10 carbon atoms, or a linear or branched dihydroxyalkyl group having 3 to 10 carbon atoms.

12. A deodorant or antiperspirant formulation, comprising at least one phosphoric ester according to claim 1.

13. A cosmetic, pharmaceutical or dermatological composition, comprising at least one phosphoric ester according to claim 1.

14. A composition according to claim 13 in the form of an aqueous, aqueous-alcoholic or aqueous-surfactant composition, in the form of an emulsion, in the form of a suspension, in the form of a dispersion, in the form of a powder or in the form of a spray.

15. A composition according to claim 13 having a pH in the range from 2 to 10.

16. A composition according to claim 13, having a pH in the range from 2.5 to 5 further comprising, based on the entire composition, from 0.05% to 3.0% by weight, of at least one organic acid having an antimicrobial effect.

17. A composition according to claim 13, further comprising at least one electrolyte.

18. A composition according to claim 17, wherein the at least one electrolyte is from 0.1% to 20.0% by weight, based on the entire composition.

19. A composition according to claim 13, further comprising hydrogen peroxide or hydrogen peroxide releasers.

20. A composition according to claim 13, wherein the at least one is present in an amount of 0.01% to 10.0% by weight, based on the final composition.

21. A composition according to claim 13, further comprising at least one surfactant.

* * * * *